US007718697B2

(12) United States Patent
Drace et al.

(10) Patent No.: US 7,718,697 B2
(45) Date of Patent: May 18, 2010

(54) METHOD FOR TREATING GLAUCOMA COMPRISING ADMINISTERING α-LIPOIC ACID

(75) Inventors: Colene D. Drace, Fort Worth, TX (US); Gary W. Williams, Burleson, TX (US); Curtis R. Kelly, Arlington, TX (US); Najam A. Sharif, Keller, TX (US)

(73) Assignee: Alcon, Inc., Hunenberg (CH)

( * ) Notice: Subject to any disclaimer, the term of this patent is extended or adjusted under 35 U.S.C. 154(b) by 1280 days.

(21) Appl. No.: 11/006,007

(22) Filed: Dec. 7, 2004

(65) Prior Publication Data
US 2005/0137123 A1 Jun. 23, 2005

Related U.S. Application Data

(60) Provisional application No. 60/530,436, filed on Dec. 17, 2003.

(51) Int. Cl.
*A61K 31/19* (2006.01)
(52) U.S. Cl. ..................................... 514/557
(58) Field of Classification Search .................. None
See application file for complete search history.

(56) References Cited

U.S. PATENT DOCUMENTS

| 5,145,871 | A | * | 9/1992 | Cavazza ..................... 514/546 |
| 5,288,735 | A | * | 2/1994 | Trager et al. ................ 514/363 |
| 5,364,884 | A | * | 11/1994 | Varma et al. ................ 514/551 |
| 2002/0102581 | A1 | | 8/2002 | Hageman et al. |
| 2004/0104646 | A1 | | 6/2004 | Kelly et al. |

FOREIGN PATENT DOCUMENTS

WO        WO02/20028        *    3/2002

OTHER PUBLICATIONS

Gutteridge, Clinical and Exp. Optometry, vol. 83, 161-172, 2000.*
Filina et al., Vestn. Oftalmol. 1995 as printed by the Examiner from [www.ncbi.nlm.gov/pubmed]. pubmed# 8604540 obtained on Apr. 16, 2009, p. 1-2.*
Filina et al English Trnaslation: An English translation of Felina et al. Vestn. Oflalmol. 1995 by USPTO-STIC (PTO-09-4740), pp. 1-11.*
Lipoic acid: Medical Subject Headings printed by the Examiner from [www.nlm.nih.gov/cgi/mesh/2009] on Apr. 16, 2009, pp. 1-3.*
Abler, et al., Commun. Mol. Path. & Pharm. 92:177-189 (1996).
Ambati, J., et al., Surv. Ophthalmol. 48:257-293 (2003).
Asrani and Zeimer, Br. J. Ophthalm. 79(8):776-780 (1995).
Asrani, et al., Inv. Ophthalm. Vis. Sci. 38(13):2702-2710 (1997).
Bengtsson, Br J Ophthalmol, vol. 73, pp. 483-487 (1989).
Bressler, et al., Sur. Ophthalm, 32:375-413 (1988).
Brown, M., Drug Discov. Today 8:474-475 (2003).
Burns and Duff, Neurochem Res. 28:979-986 (2003).
Caricasole, A., et al., Trends Pharmacol. Sci. 24:233-238 (2003).
Chabry, J., et al., J. Neurosci. 23:462-469 (2003).
Chang, B-D., et al., Proc. Nat. Acad. Sci., USA 97:4291-4296 (2000).
Ciulla, et al., Sur. Ophthalm. 43:134-146 (1988).
Curcio, et al., Inv. Ophthalm. Vis. Sci. 37:1236-1249 (1996).
Damiens et al., Oncogene, 20(29):3786-3797 (2001).
Eldar-Finkelman, H., Trends Mol. Med. 8:126-132 (2002).
Ermilov et al., Arkh Patol, "Senile amyloidosis of the eye as a manifestation of senile cerebral amyloidosis", 43-45 (Russian) (1993).
Fakforovich, et al., Nature 347:83-86 (1990).
Frankiewicz and Parsons, Neuropharmacol. 38:1253-1259 (1999).
Ge-Zhi, et al., Trans. Am. Ophthalm. Soc. 94:411-430 (1996).
Gragoudas, et al., Inv. Ophthalm, Vis. Sci. 38(4)S17 (1997).
Gupta-Bansal and Brunden, J. Neurochem. 70:292-298 (1998).
Hock, C., et al., Amyloid: J. Prot. Fold. Disord. 10:1-6 (2003).
Husain, et al., Ophthalm. 104(8):1242-1250 (1997).
Janus, C., et al., Nature 408:979-982 (2000).
Jen, LS., et al., Nature 392:140-141 (1998).
Jensen, LE and Whitehead, AS, Biochem. J. 334:489-503 (1998).
Johan, K., et al., Proc. Nat. Acad. Sci. USA 95:2558-2563 (1998).
Kane, M.D., et al., J. Neurochem. 72:1939-1949 (1999).
Kindy, M.D., et al., J. Alzheimer's Disease 1:155-167 (1999).
Koriyama, Y., et al., Eur. J. Pharmacol. 458:235-241 (2003).
Krasnov, Vestn Oftalmol, "Morphological features of senile and secondary amyloidosis of the iris and sclera in patients with glaucoma" abstract (Jan.-Mar. 1996).
Kumon, Y., et al., Scand. J. Immunol. 53:7-12 (2001).
Kumon, Y., et al., Amyloid 9:237-241 (2002).
Kumon, Y., et al., Scand. J. Immunol. 56:504-511 (2002).
Lambert, M.P., et al., Proc. Nat. Acad. Sci. USA 95:6448-6453 (1998).
Lanz, T.A., et al., J. Pharmacol. Expt. Ther. 305:864-871 (2003).
LaVail, et al., Proc. Nat. Acad. Sci. 89:11249-11253 (1992).
Leske, M.C., et al., American Journal of Epidemilogy, 118(2):166-191 (Aug. 1983).
Liang, J.S., et al., Neurosci. Lett. 225:73-76 (1997).
Lin, et al., Curr. Eye Res. 13(7):513-522 (1994).
Liu, Y., et al., J. Neurochem. 69:2285-2293 (1997).
Marks, N. and Berg, M.J., Neurochem. Res. 28:1049-1062 (2003).
Matsuoka, Y., et al., J. Neurosci. 23:29-33 (2003).
Miida, T., et al., Biochem. 38(51):16958-16962 (1999).
Morgan, D., et al., Nature 408:982-985 (2000).
Naash, et al., Inv. Ophthalm, Vis. Sci. 37:775-782 (1996).
Nakagami, Y. and Oda, T., Jpn. J. Pharmacol. 88:223-226 (2002).
Nakagami, Y., et al., Br. J. Pharmacol. 137:676-682 (2002).
Nakagami et al., Eur J P, 457:11-17 (2002).
Noell, et al., Invest. Ophthalm. Vis. Sci. 5:450-472 (1966).
O'Hara, R., et al., Arthritis Res. 2:142 (2000).
Pike, C.J., et al., J. Neurosci. 13:1676-1687 (1993).
Schenk, D., et al., Nature 400:173-177 (1999).
Schwartz et al., Ophthalmology, 89(4):394-401 (1982).
Sickenberg, et al., Inv. Ophthalm. Vis. Sci. 38(4):S92 (1997).

(Continued)

*Primary Examiner*—Robert Landsman
*Assistant Examiner*—Gyan Chandra
(74) *Attorney, Agent, or Firm*—Teresa J. Schultz

(57) ABSTRACT

The present invention provides compositions and methods for treating glaucoma, ocular hypertension, and age-related macular degeneration. More specifically, the present invention describes the use of agents that down-regulate expression of tanis and/or p21$^{Waf1/Cip1/Sd1}$ genes to treat such disorders of the eye.

1 Claim, No Drawings

OTHER PUBLICATIONS

Strong, N. P., "How optometrists screen for glaucoma: A survey", Ophthal. Physiol. Opt., 12:3-7 (1992).
Taylor, et al., Arch. Ophthalm. 110:99-104 (1992).
Thomas, et al., Inv. Ophthalm. Vis. Sci. 39(4):S242 (1998).
Thorn, C.F., et al., J. Immunol. 169:399-406 (2002).
Uhlar, C.M., et al., Eur. J. Biochem. 265:501-523 (1999).
Urieli-Shoval, S., et al., J. Histochem. Cytochem. 46:1377-1384 (1998).
Vaughan, D. et al., In: General Ophthalmology, Appleton & Lange, Norwalk, Conn., pp. 213-230 (1992).
Walder, et al., Diabetes 51:1859-1866 (2002).
Xia, W., Drug News Perspect. 16:69-73 (2003).
Xiang et al., (2002) Neurobiol. Aging 23:327-334.
Yamada, et al., Scand. J. Immunol. 52:7-12 (2000).
Yamazaki, et al., Biochemical and Biophysical Res. Comm. 290:1114-1122 (2002).
Yankner et al., Science, 250:279-282 (1990).
Young, Sur. Ophthalm. 32:252-269 (1988).
Zhang, L., et al., Neurosci. Lett. 312:125-128 (2001).

* cited by examiner

METHOD FOR TREATING GLAUCOMA COMPRISING ADMINISTERING α-LIPOIC ACID

This application claims priority from the provisional application, U.S. Patent Application Ser. No. 60/530,436 filed Dec. 17, 2003.

BACKGROUND OF THE INVENTION

1. Field of the Invention

The present invention relates to the field of diagnosis and treatment of glaucoma. More specifically, the invention provides methods and compositions for treating ocular hypertension, glaucoma and age-related macular degeneration (ARMD) and for identifying therapeutic agents to treat these blinding diseases.

2. Description of the Related Art

There are a number of ocular conditions that are caused by, or aggravated by, damage to the optic nerve head, degeneration of ocular tissues, and/or elevated intraocular pressure. For example, "glaucomas" are a group of debilitating eye diseases that are a leading cause of irreversible blindness in the United States and other developed nations. Primary Open Angle Glaucoma ("POAG") is the most common form of glaucoma. The disease is characterized by the degeneration of the trabecular meshwork, leading to obstruction of the normal ability of aqueous humor to leave the eye without closure of the space (e.g., the "angle") between the iris and cornea (Vaughan, D. et al., (1992)). A characteristic of such obstruction in this disease is an increased intraocular pressure ("IOP"), resulting in progressive visual loss and blindness if not treated appropriately and in a timely fashion. The disease is estimated to affect between 0.4% and 3.3% of all adults over 40 years old (Leske, M. C. et al. (1986); Bengtsson, B. (1989); Strong, N. P. (1992)). Moreover, the prevalence of the disease rises with age to over 6% of those 75 years or older (Strong, N. P., (1992)).

Glaucoma affects three separate tissues in the eye. The elevated IOP associated with POAG is due to morphological and biochemical changes in the trabecular meshwork (TM), a tissue located at the angle between the cornea and iris. Most of the nutritive aqueous humor exits the anterior segment of the eye through the TM. The progressive loss of TM cells and the build-up of extracellular debris in the TM of glaucomatous eyes leads to increased resistance to aqueous outflow, thereby raising IOP. Elevated IOP, as well as other factors such as ischemia, cause degenerative changes in the optic nerve head (ONH) leading to progressive "cupping" of the ONH and loss of retinal ganglion cells and axons. The detailed molecular mechanisms responsible for glaucomatous damage to the TM, ONH, and the retinal ganglion cells are unknown.

Twenty years ago, the interplay of ocular hypertension, ischemia and mechanical distortion of the optic nerve head were heavily debated as the major factors causing progression of visual field loss in glaucoma. Since then, other factors including excitotoxicity, nitric oxide, absence of vital neurotrophic factors, abnormal glial/neuronal interplay and genetics have been implicated in the degenerative disease process. The consideration of molecular genetics deserves some discussion insofar as it may ultimately define the mechanism of cell death, and provide for discrimination of the various forms of glaucoma. Within the past 8 years, over 15 different glaucoma genes have been mapped and 7 glaucoma genes identified. This includes six mapped genes (GLC1A-GLC1F) and two identified genes (MYOC and OPTN) for primary open angle glaucoma, two mapped genes (GLC3A-GLC3B) and one identified gene for congenital glaucoma (CYP1B1), two mapped genes for pigmentary dispersion/pigmentary glaucoma, and a number of genes for developmental or syndromic forms of glaucoma (FOXC1, PITX2, LMX1B, PAX6).

Thus, each form of glaucoma may have a unique pathology and accordingly a different therapeutic approach to the management of the disease may be required. For example, a drug that effects the expression of enzymes that degrade the extracellular matrix of the optic nerve head would not likely prevent RGC death caused by excitotoxicity or neurotrophic factor deficit. In glaucoma, RGC death occurs by a process called apoptosis (programmed cell death). It has been speculated that different types of insults that can cause death may do so by converging on a few common pathways. Targeting downstream at a common pathway is a strategy that may broaden the utility of a drug and increase the probability that it may have utility in the management of different forms of the disease. However, drugs that effect multiple metabolic pathways are more likely to produce undesirable side-effects. With the advent of gene-based diagnostic kits to identify specific forms of glaucoma, selective neuroprotective agents can be tested with the aim of reducing the degree of variation about the measured response.

Glaucoma is currently diagnosed based on specific signs of the disease (characteristic optic nerve head changes and visual field loss). However, over half of the population with glaucoma are unaware they have this blinding disease and by the time they are diagnosed, they already have irreversibly lost approximately 30-50% of their retinal ganglion cells. Thus, improved methods for early diagnosis of glaucoma are needed.

Current glaucoma therapy is directed to lowering IOP, a major risk factor for the development and progression of glaucoma. However, none of the current IOP lowering therapies actually intervenes in the glaucomatous disease process responsible for elevated IOP and progressive damage to the anterior segment continues. This is one possible reason why most patients become "resistant" to conventional glaucoma therapies. Thus, what is needed is a therapeutic method for altering (by inhibiting or even reversing) the disease process.

Another blinding disease is age-related macular degeneration (ARMD) that affects the outer retina, retinal pigmented epithelial cells, Bruch's membrane, and the choroid. (Ambati et al. 2003). The hallmarks of this disease are diffuse and focal thickening of the Bruch's membrane due to deposition of lipoproteins (drusen) leading to retinal dysfunction culminating in retinal detachment and loss of vision. Other lipoproteins, such as Tanis gene receptor and SAA, may also be deposited at the Bruch's membrane to exacerbate the pathology and retinal dysfunction.

There are several reports suggesting that primary amyloidosis may be associated with glaucoma. For example, it was found that amyloid was deposited in various ocular tissues including the vitreous, retina, choroid, iris, lens, and trabecular meshwork in primary systemic amyloidosis patients (Schwartz et al. 1982). Ermilov et al. (1993) reported that in 478 eyes of 313 patients (aged 25 years to 90 years) with cataracts, glaucoma, and/or diabetes mellitus, 66 (14%) of the eyes contained amyloid-pseudoexfoliative amyloid (PEA) proteins. Krasnov et al. (1996) reported that 44.4% of 115 patients with open-angle glaucoma revealed extracellular depositions of amyloid proteins. Finally, amyloidosis was revealed in the sclera in 82% of the cases and in the iris in 70% of the cases. A number of clinical conditions, including Alzheimer's disease, exhibit abnormal amyloid deposits in tissues associated with the disease. However, amyloids are molecularly heterogeneous and encoded by different amyloid genes. The previous reports are unclear regarding which amyloid(s) might be associated with glaucoma.

To date, more than 100 genes have been mapped or cloned that may be associated with retinal degeneration. The pathogenesis of retinal degenerative diseases such as age-related macular degeneration (ARMD) and retinitis pigmentosa (RP) is multifaceted and can be triggered by environmental factors in those who are genetically predisposed. One such environmental factor, light exposure, has been identified as a contributing factor to the progression of retinal degenerative disorders such as ARMD (Young 1988). Photo-oxidative stress leading to light damage to retinal cells has been shown to be a useful model for studying retinal degenerative diseases for the following reasons: damage is primarily to the photoreceptors and retinal pigment epithelium (RPE) of the outer retina (Noell et al. 1966; Bressler et al. 1988; Curcio et al. 1996); they share a common mechanism of cell death, apoptosis (Ge-Zhi, et al. 1996; Abler et al. 1996); light has been implicated as an environmental risk factor for progression of ARMD and RP (Taylor et al. 1992; Naash et al. 1996); and therapeutic interventions which inhibit photo-oxidative injury have also been shown to be effective in animal models of neurodegenerative retinal disease (LaVail et al. 1992; Fakforovich et al. 1990).

To date, there are no approved effective therapies for the treatment of ocular neovascular diseases which do not include the destruction of healthy viable tissue. There are certainly no therapies specifically directed at eliminating or inhibiting the deposition and accumulation of amyloid proteins, drusen or amyloid-like proteins including SAA on the Bruch's membrane in the retina as in ARMD. Such accumulation of amyloid and/or drusen and other lipoproteins including SAA causes retinal dysfunction by several mechanisms including disruption of retinal pigmented epithelial (RPE) cell function due to thickening of Bruch's membrane, and RPE detachment resulting in rapid loss of visual acuity followed by macular atrophy and retinal detachment (Ciulla et al. 1998). Additionally, the deposited drusen and/or amyloid proteins including SAA could exert direct neurotoxic effects on the RPE cells and neighboring cells in the retina akin to the well known toxic effects of such amyloid proteins and amyloid/lipid complexes observed in brain cell death as in Alzheimer's disease (Lambert et al. 1998; Liu and Schubert 1997; Pike et al. 1993; Nakagami et al. 2002) in retina (Jen et al. 1998). Although panretinal photocoagulation is the current medical practice for the treatment of diabetic retinopathy and ARMD and is effective in inhibiting retinal neovascularization, this procedure destroys healthy peripheral retinal tissue. This destruction of healthy tissue decreases the retinal metabolic demand and thereby reduces retinal ischemia driven neovascularization. Photodynamic therapy (PDT) is a procedure in which a photoactivatable dye is given systemically followed by laser activation of the dye in the eye at the site of new blood vessel formation (Asrani & Zeimer 1995; Asrani et al. 1997; Husain et al. 1997; Lin et al. 1994). The photoactivated drug generates free oxygen radicals which seal the newly formed blood vessels and thereby prevent or reduce their growth, at least temporarily. This procedure has been used in patients with the exudative form of macular degeneration and many patients show regression of their subretinal neovascular membranes. Unfortunately, it appears that the PDT-induced inhibition of retinal neovascularization is risky, expensive and provides transient and temporary relief lasting only 6-12 weeks (Gragoudas et al. 1997; Sickenberg et al. 1997; Thomas et al. 1998).

Thus, there is an urgent need for therapeutic methods for altering (by inhibiting or even reversing) the disease processes of glaucoma and ARMD.

SUMMARY OF THE INVENTION

The present invention overcomes these and other drawbacks of the prior art by providing methods to diagnose and compositions to treat ocular hypertension, glaucoma and ARMD. The present invention overcomes these and other drawbacks of the prior art by providing compositions and methods for treating ARMD by sequestering and/or degrading Tanis gene product protein (TGPP) and/or p21$^{Waf1/Cop1/Sdi1}$ gene product protein (p21GPP) in ocular tissues at the back of the eye, specifically at the Bruch's membrane, outer retina, macula and sub-retinal space. In addition, compositions and methods to prevent the generation of TGPP and/or p21GPP and/or to prevent the neurotoxic effects of such gene product proteins are provided to treat ARMD. In one aspect, the present invention provides a method for treating ARMD by administering to a patient in need thereof a therapeutically effective amount of a composition comprising an agent that sequesters TGPP or p21GPP in ocular tissue and/or an agent that degrades TGPP or p21GPP in ocular tissue. Such sequestration and/or degradation modulates the expression of the TGPP and p21GPP, such that the patient's condition is treated. In addition, agents that stop or reduce the initial activation of Tanis and p21$^{Waf1/Cop1/Sdi1}$ genes and/or prevent nerve cell death due to the presence of TGPP or p21GPP would also be useful to treat the patient's ARMD condition. In preferred embodiments, the agent will be a small molecular weight molecule, antibody, protein, peptide, peptidomimetic, or nucleic acid.

Preferably, the agents for use in the compositions and methods of the present invention will mainly be chosen from the following:

Compounds that may be useful for preventing the production of TGPP or p21GPP would include: γ-secretase inhibitors such as talsaclidine (Hock et al. 2003), Xanomeline, 3-(2-6-chloropyrazinyl)-1-azabicyclo(2.2.2)octane (L-689660), 1-benzyl-4-(1-(1 carbamoyl-2-phenylethylcarbamoyl-3-methylbutylcarbamoyl)-2-hydroxy-5-phenylpentyl)carbamic acid tert-butyl ester (L-685458), (4-(m-Chlorophenylcarbamoyloxy)-2-butynyl)trimethylammonium Chloride (McN-A-343), 5-propargyloxycarbonyl-1,4,5,6-tetrahydropyrimidine hydrochloride (CDD-0097), fenchylamine, Z-leu-leu-leu-CHO (MG132), Boc-PheΨPhe-Leu-Val-OMe (WPE-111-31C, where Ψ is the pseudopeptide bond containing the hydroxyethyl group), (MW-11-36C/26A), Boc-Val-Ile-NH—CH(CH$_3$)—C(=O)—CH(F$_2$)—C(=O)—NH-Val-Ile-OMe (MW-167), CM-265, lactacystin, DNPS1 and N—[N-(3,5-difluorophenacetyl)-L-alanyl]-S-phenylglycine t-butyl ester (DAFT) (Lanz et al. 2003). Other compounds of use may include the statin family, e.g. pravastatin, atorvastatin (see Burns and Duff 2003) and presenilinase inhibitors such as pepstatin A (Xia 2003) and talsaclidine (Hock et al. 2003).

Compounds that may be useful for promoting degradation of TGPP or p21GPP may include glycoaminoglycans and congo red (*J. Neurochem.* 70: 292-298 [1998]).

Compounds that may be useful for promoting sequestration or clearance of TGPP or p21GPP may include gelsolin and ganglioside GM1 (Matsuoka et al. 2003). In addition, antibodies raised against drusen, and/or amyloid proteins and/or against amyloid-like proteins would be useful for sequestration and clearance of the former detrimental proteins as has been shown in the brain (Schenk et al. 1999; Janus et al. 2000; Morgan et al. 2000).

Compounds that may be useful for preventing or diminishing the neurotoxic effects of TGPP or p21GPP include RS-0466 (Nakagami et al. 2002c; Nakagami et al. 2002b), V-type ATPase inhibitors (bafilomycin and concanamycin; Kane et al. 1999), tachykinin peptides and their non-peptide analogs (Yankner et al. 1990), α-lipoic acid (Zhang et al. 2001), propentofylline (Koriyama et al. 2003), glycogen synthase kinase-3β (GSK-3β) inhibitors (Eldar-Finkelman 2002; Caricasole et al. 2003), memantine (Frankiewicz and Parsons 1999), mixed cyclin-dependent kinase-GSK3β inhibitors (Damiens et al. 2001), COX-2 inhibitors (Xiang et al. 2002) and propentofylline (Koriyama et al. 2003).

The present invention further provides a method of treating glaucoma by administering a composition containing a p21$^{Waf1/Cip/Sdi1}$ gene product protein (see below) inhibitor and/or inhibitors of CDK1, CDK2, CDK5 and CDK9, and inhibitors of cJAK and ASRK-1 including the following agents: olomoucine, roscovitine, purvalanol, kenpaullone, alsterpaullone, indirubins, flavopiridol, stauroporine and analogs and derivatives of the above compounds.

In one aspect, the present invention provides a method for treating glaucoma by administering to a patient in need thereof a therapeutically effective amount of a composition comprising an agent that interacts with a gene encoding a serum amyloid A (SAA) receptor (SEQ ID NO:12), wherein said interaction decreases the expression of SAA (SEQ ID NO:1).

In another aspect, the present invention provides a method for treating glaucoma by administering to a patient in need thereof a therapeutically effective amount of a composition comprising a Tanis antagonist.

In preferred aspects, the agent for use in the methods of the invention is a peroxisome proliferator-activated receptor α (PPARα) agonist, tachykinin peptide or non-peptide analogs thereof, or α-lipoic acid. More preferably, the agent is fenofibrate, Wy-14643, (4-chloro-6-(2,3-xylidino)-2-pryrimidinylthiol)-acetic acid), ciprofibrate, 2-bromohexadecanoic acid, bezafibrate and ciglitizone, bafilomycin or concanamycin.

In yet another aspect, the invention provides a method for treating glaucoma by administering to a patient in need thereof a therapeutically effective amount of a composition comprising a p21 antagonist.

The present invention further provides a pharmaceutical composition comprising a therapeutically effective amount of a Tanis antagonist and a pharmaceutical carrier.

DETAILED DESCRIPTION PREFERRED EMBODIMENTS

Glaucoma is a heterogeneous group of optic neuropathies that share certain clinical features. The loss of vision in glaucoma is due to the selective death of retinal ganglion cells in the neural retina that is clinically diagnosed by characteristic changes in the visual field, nerve fiber layer defects, and a progressive cupping of the ONH. One of the main risk factors for the development of glaucoma is the presence of ocular hypertension (elevated intraocular pressure, IOP). IOP also appears to be involved in the pathogenesis of normal tension glaucoma where patients have what is often considered to be normal IOP. The elevated IOP associated with glaucoma is due to elevated aqueous humor outflow resistance in the trabecular meshwork (TM), a small specialized tissue located in the iris-corneal angle of the ocular anterior chamber. Glaucomatous changes to the TM include a loss in TM cells and the deposition and accumulation of extracellular debris including proteinaceous plaque-like material. In addition, there are also changes that occur in the glaucomatous optic nerve head (ONH). In glaucomatous eyes, there are morphological and mobility changes in ONH glial cells. In response to elevated IOP and/or transient ischemic insults, there is a change in the composition of the ONH extracellular matrix and alterations in the glial cell and retinal ganglion cell axon morphologies.

It has been found that the expression of Serum Amyloid A (SAA) mRNA is significantly upregulated in glaucomatous TM tissues and cells. The differential expression seen has been verified using Affymetrix gene chips by real time quantitative polymerase chain reaction (QPCR). This is the first time SAA has been shown to be expressed in the TM (U.S. application Ser. No. 60/530,430).

Human SAA comprises a number of small, differentially expressed apolipoproteins encoded by genes localized on the short arm of chromosome 11. There are four isoforms of SAAs. SAA1 (SEQ ID NO:2), encoded by SEQ ID NO:1, and SAA2 (SEQ ID NO:4), encoded by SEQ ID NO:3, are known as acute phase reactants, like C-reactive protein, that is, they are dramatically upregulated by proinflammatory cytokines. The 5'UTR promoter regions of SAA1 and SAA2 genes are also provided (SEQ ID NO:12 and SEQ ID NO:13, respectively). SAA3 (SEQ ID NO:5) is a pseudogene and SAA4 (SEQ ID NO:6) is a low level endogenously expressed gene encoding endogenous SAA4 (SEQ ID NO:7). SAA2 has two isoforms, SAA2α (SEQ ID NO:9), encoded by SEQ ID NO:8, and SAA2β (SEQ ID NO:11), encoded by SEQ ID NO:10, which differ by only one amino acid. SAA1 and SAA2 proteins are 93.5% identical at the amino acid level (SEQ ID NO:2 and SEQ ID NO:4, respectively) and these genes are 96.7% identical at the nucleotide level (SEQ ID NO:1 and SEQ ID NO:3, respectively).

SAA functions as an apolipoprotein and is expressed in a number of tissues in addition to the liver (Miida et al. 1999). However, over-expression of SAA1 or SAA2 leads to the formation of linear fibrils in amyloid deposits, which can lead to pathogenesis and thus many types of diseases (Uhlar and Whitehead 1999; Liang et al. 1997). SAA plays an important role in infections, inflammation, and in the stimulation of tissue repair. SAA concentration may increase up to 1000-fold following inflammation, infection, necrosis, and decline rapidly following recovery. Thus, serum SAA concentration is considered to be a useful marker with which to monitor inflammatory disease activity. Hepatic biosynthesis of SAA is up-regulated by pro-inflammatory cytokines, leading to an acute phase response. Chronically elevated SAA concentrations are a prerequisite for the pathogenesis of secondary amyloidosis, a progressive and sometimes fatal disease characterized by the deposition in major organs of insoluble plaques composed principally of proteolytically cleaved SAA. This same process also may lead to atherosclerosis. There is a requirement for both positive and negative SAA control mechanisms to maintain homeostasis. These mechanisms permit the rapid induction of SAA expression to fulfill host-protective functions, but they also must ensure that SAA expression is rapidly returned to baseline levels to prevent amyloidosis. These mechanisms include modulation of promoter activity involving, for example, the inducer nuclear factor kB (NF-kB) and its inhibitor IkB, up-regulation of transcription factors of the nuclear factor for interleukin-6 (NF-IL6) family, and transcriptional repressors such as yin and yang 1 (YY1). Post-transcriptional modulation involving changes in mRNA stability and translation efficiency permit further up- and down-regulatory control of SAA protein synthesis to be achieved. In the later stages of the AP response, SAA expression is effectively down-regulated via the increased production of cytokine antagonists such as the interleukin-1 receptor antagonist (IL-1Ra) and of soluble cytokine receptors, resulting in less signal transduction driven by pro-inflammatory cytokines (Jensen and Whitehead, 1998).

There are several reports suggesting that primary amyloidosis may be associated with glaucoma. For example, it was found that amyloid was deposited in various ocular tissues including the vitreous, retina, choroid, iris, lens, and TM in primary systemic amyloidosis patients (Schwartz et al. 1982). Ermilov et al. (1993) reported that in 478 eyes of 313 patients, aged 25 years to 90 years, with cataracts, glaucoma, and/or diabetes mellitus, 66 (14%) of the eyes contained amyloid-pseudoexfoliative amyloid (PEA). Krasnov et al. (1996) reported that 44.4% of 115 patients with open-angle glaucoma revealed extracellular depositions of amyloid. Amyloidosis was revealed in the sclera in 82% of the cases and in the iris in 70% of the cases. A number of clinical conditions, including Alzheimer's disease, exhibit aberrant amyloid tissue deposits associated with disease. However, amyloids are molecularly heterogeneous and encoded by different amyloid genes. The previous reports are unclear regarding which amyloid(s) are associated with glaucoma.

SAA gene expression is elevated significantly in glaucomatous TM tissues. Increased SAA may be involved in the generation of elevated IOP and damage to the optic nerve leading to vision loss in glaucoma patients.

The Tanis gene (SEQ ID NO:14) is a recently identified gene that encodes a membrane protein (SEQ ID NO:15) said to bind to SAA (Walder et al. 2002). It is believed that therapeutic intervention of the interaction between SAA and its putative receptor, encoded by the Tanis gene, may modulate SAA expression levels and/or receptor-mediated SAA signaling. Methods for the identification of agents that interfere with this interaction and their use for the treatment of ocular hypertension, glaucoma and ARMD are also provided herein.

It has also recently been discovered that a gene called $p21^{Waf1/Cip/Sdi1}$ (SEQ ID NO:16) activates SAA and activates the gene APP that produces amyloid protein which forms plaques in the brain that are hallmarks of Alzheimer's disease (Chang et al 2000; Kindy et al. 1999; Johan et al. 1997). In addition, $p21^{Waf1/Cip/Sdi1}$-induced gene expression results in over production of extracellular matrix (ECM) proteins including fibronectin-1, plasminogen activator inhibitor, tissue-type plasminogen activator, integrin β3 (Chang et al. 2000) which may be contributive factors in the glaucomatous situation. Likewise, $p21^{Waf1/Cip/Sdi1}$-induced connective tissue growth factor and galectin-3 (Chang et al. 2000) may also play significant roles in deposition of ECM proteins and other components of ECM in the anterior eye segment leading to ocular hypertension and glaucoma. Therefore, it is believed that inhibition of $p21^{Waf1/Cip/Sdi1}$ gene would be useful in the treatment of the pathophysiology of glaucoma. Interestingly, since $p21^{Waf1/Cip/Sdi1}$ gene expression results in natural inhibition of cyclin-dependent kinases (CDK) (Chang et al. 2000), and since $p21^{Waf1/Cip/Sdi1}$ was reported to bind c-Jun amino-terminal kinase (cJAK), apoptosis-signal-regulating kinase 1 (ASRK-1) and Gadd45 (Chang et al. 2000), it follows that inhibitors of these kinases would also act as $p21^{Waf1/Cip/Sdi1}$ antagonists. Accordingly, inhibitors of CDK1, 2, 5 and 9, and inhibitors of cJAK and ASRK-1 would be useful for treating ocular hypertension, glaucoma and ARMD. Agents which may modulate the interaction of SAA and its putative receptor and the TGPP or p21GPP include, but are not limited to, peroxisome proliferator-activated receptor α (PPARα) agonists, tachykinin peptides and their non-peptide analogs, and α-lipoic acid. PPARα agonists include arachidonic acid, linoleic acid, docosahexaenoic acid, eicosapentaenoic acid, 8(S)-HETE, (±)ibuprofin, indomethacin, leukotriene $B_4$, meclofenamate, prostaglandin $A_1$, prostaglandin $A_2$, prostaglandin $D_1$, prostaglandin $D_2$, prostaglandin $J_2$, 15-deoxy-$\Delta^{12}$-prostaglandin $J_2$, WY 14643, ciglitizone, carbaprostacyclin and prostacyclin. Examples of preferred agents for use in the present invention include fenofibrate, WY 14643, (4-chloro-6-(2,3-xylidino)-2-pryrimidinylthiol)-acetic acid), ciprofibrate, 2-bromohexadecanoic acid, bezafibrate, ciglitizone, bafilomycin, and concanamycin.

In another aspect the present invention provides a pharmaceutical composition comprising a therapeutically effective amount of a Tanis gene product protein inhibitor and/or Tani gene inhibitor or a $p21^{Waf1/Cip/Sdi1}$ gene inhibitor or $p21^{Waf1/Cip/Sdi1}$ gene product protein inhibitor and a pharmaceutical carrier.

The Compounds of this invention, can be incorporated into various types of ophthalmic formulations for delivery to the eye (e.g., topically, intracamerally, or via an implant). The Compounds are preferably incorporated into topical ophthalmic formulations for delivery to the eye. The Compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a Compound in a physiologically acceptable isotonic aqueous buffer. Further, the ophthalmic solution may include an ophthalmologically acceptable surfactant to assist in dissolving the Compound. Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the Compound in a hydrophilic base prepared from the combination of, for example, carbopol-974, or the like, according to the published formulations for analogous ophthalmic preparations; preservatives and tonicity agents can be incorporated.

The Compounds are preferably formulated as topical ophthalmic suspensions or solutions, with a pH of about 4 to 8. The establishment of a specific dosage regimen for each individual is left to the discretion of the clinicians. The Compounds will normally be contained in these formulations in an amount 0.01% to 5% by weight, but preferably in an amount of 0.05% to 2% and most preferably in an amount 0.1 to 1.0% by weight. The dosage form may be a solution, suspension microemulsion. Thus, for topical presentation 1 to 2 drops of these formulations would be delivered to the surface of the eye 1 to 4 times per day according to the discretion of a skilled clinician.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Formulation of Tanis Gene (TG) Inhibitor or TG Product Protein Inhibitor or p21$^{Waf1/Cip/Sdi1}$ Gene Inhibitor or Inhibitor of p21$^{Waf1/Cip/Sdi1}$ Gene Product Protein for Topical Ocular Application 1% suspension or solution of Tanis gene inhibitor (TGI) or inhibitor of Tanis gene product protein (TGPPI) or p21$^{Waf1/Cip/Sdi1}$ gene inhibitor (p21GI) or inhibitor of p21G product protein (p21GPPI) for topical ocular application:

| Description | Conc. | Units | Purpose |
| --- | --- | --- | --- |
| TGI or TGPPI or p21GI or p21GPPI | 1% | W/V% | active ingredient |
| hydroxypropyl methylcellulose | 0.5% | W/V % | viscosity modifier (2910) (E4M), USP |
| dibasic sodium phosphate (anhydrous), usp | 0.2% | W/V % | buffering agent |
| sodium chloride, usp | 0.75% | W/V % | tonicity agent |
| disodium edta (edetate disodium), usp | 0.01% | W/V % | chelating agent |
| polysorbate 80, nf | 0.05% | W/V % | wetting agent |
| benzalkonium chloride, nf | 0.01% | W/V % | preservative |
| sodium hydroxide, nf | q.s. pH | W/V % | pH adjust |
| hydrochloric acid, nf | q.s. pH | W/V % | pH adjust |
| purified water, usp | q.s. 100% | W/V % | vehicle |

In similar other examples, TGI or TGPPI or p21GI or p21GPPI will be substituted by agents that sequester or degrade the above or agents that prevent the toxic effects of the above.

Methods to measure the potency or efficacy of agents that can inhibit the secretion of SAA from cultured cells involve the use of an enzyme-linked immunosorbant assay (ELISA) for human SAA as described by Yamada et al. (2000) and using human peripheral monocytes and monocytic leukaemic cell-line THP-1. In addition, methods to determine the potency and efficacy of agents to inhibit gene expression of p21$^{Waf1/Cip/Sdi1}$ can be studies using standard methods described by Chang et al. (2000).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The following references, and the bibliography cited within these, to the extent that they provide exemplary procedural or other details supplementary to those set forth herein, are specifically incorporated herein by reference.

PUBLICATIONS

Abler et al., RES. COMMUN. MOL. PATH. & PHARM. 92:177-189 (1996).

Ambati, J. et al., *Age-related macular degeneration: etiology, pathogenesis, and therapeuic strategies*. Surv. Ophthalmol. 48: 257-293 (2003).

Asrani et al., INV. OPHTHALM. VIS. SCI. 38(13):2702-2710 (1997).

Asrani and Zeimer, BR. J. OPHTHALM. 79(8):776-780 (1995).

Bressler et al., SUR. OPHTHALM. 32:375-413 (1988).

Brown, M., *Gene therapy success for Alzheimer's?* DRUG DISCOV. TODAY 8:474-475 (2003).

Caricasole, A. et al., *The Wnt pathway, cell-cycle activation and β-amyloid; novel therapeutic strategies in Alzheimer's disease?* TRENDS PHARMACOL. SCI. 24:233-238 (2003).

Chabry J. et al., *In vivo and in vitro neurotoxicity of the human prion protein (PrP) fragment P1118-135 independently of the PrP expression*, J. NEUROSCI. 23:462-469 (2003).

Chang, B-D. et al., *Effects of p21$^{Waf1/Cip/Sdi1}$ on cellular gene expression: implications for carcinogensis, senescence, and age-related diseases*, PROC. NAT. ACAD. SCI, USA 97:4291-4296 (2000).

Ciulla et al., SUR. OPHTHALM. 43:134-146 (1988).

Curcio et al., INV. OPHTHALM. VIS. SCI. 37:1236-1249 (1996).

Fakforovich et al., NATURE 347:83-86 (1990).

Ge-Zhi et al., TRANS. AM. OPHTHALM. SOC. 94:411-430 (1996).

Gragoudas et al., INV. OPHTHALM. VIS. SCI. 38(4)S17 (1997).

Hock, C. et al., *Treatment with the selective muscarinic m1 agonist talsaclidine decreases cerebrospinal fluid levels of Aβ$_{42}$ in patients with Alzheimer's disease*, AMYLOID: J. PROT. FOLD. DISORD. 10:1-6 (2003).

Husain et al., OPHTHALM. 104(8):242-250 (1997).

Janus, C. et al., *Aβ peptide immunization reduces behavioural impairment and plaques in a model of Alzheimer's disease*, NATURE 408:979-982 (2000).

Jen, L. S. et al., *Alzheimer's peptide kills cells of retina in vivo*, NATURE 392:140-141 (1998).

Jensen L E and Whitehead A S, BIOCHEM. J. 334:489-503 (1998).

Johan, K. et al., *Acceleration of amyloid protein A amyloidosis by amyloid-like synthetic fibrils*, PROC. NAT. ACAD. SCI USA 95:2558-268 (1997).

Kane, M. D. et al., *Inhibitors of V-type ATPases, bafilomycin A1 and concanamycin A, protect against β-amyloid-mediated effects on 3-(4,5-dimethylthiazol-2-yl)-2,5-diphenyltetrazolium bromide (MTT) reduction*, J. NEUROCHEM. 72:1939-1947 (1999).

Kindy, M. S et al., *Apolipoprotein serum amyloid A in Alzheimer's disease*, J. ALZHEIMER'S DISEASE 1:155-167 (1999).

Koriyama, Y. et al., *Propentofylline protects β-amyloid protein-induced apoptosis in cultured rat hippocampal neurons* EUR. J. PHARMACOL. 458:235-241 (2003).

Kumon, Y., Hosokawa, T., Suchiro, T., Ideda, Y., Sipe, J. D., and Hashimoto, K., *Acute-phase, but not constitutive serum amyloid A (SAA) is chemotactic for cultured human aortic smooth muscle cells*, AMYLOID 9:237-241 (2002a).

Kumon, Y., Suchiro, T., Faulkes, D. J., Hosakawa, T., Ideda, Y., Woo, P., Sipe, J. D., and Hashimoto, K., *Transcriptional regulation of Serum Amyloid A1 gene expression in human aortic smooth muscle cells involves CCAAT/enhancer binding proteins (C/EBP) and is distinct from HepG2 cells*, SCAND. J. IMMUNOL. 56:504-511 (2002b).

Kumon, Y., Suchiro, T., Hashimoto, K., and Sipe, J. D., *Dexamethasone, but not IL-1 alone, upregulates acute-phase serum amyloid A gene expression and production by cultured human aortic smooth muscle cells*, SCAND J. IMMUNOL. 53:7-12 (2001).

Lambert, M. P. et al., *Diffusible, nonfibrillar ligands derived form Aβ$_{1-42}$ are potent central nervous system neurotoxins*, PROC. NAT. ACAD. SCI. USA 95:6448-6453 (1998).

Lanz, T. A. et al., *The γ-secretase inhibitor N-(N-(3,5-difluorophenacetyl)-L-alanyl]-S-phenylglycine t-butyl ester reduces Aβ levels in vivo in plasma and cerebrospinal fluid* in young (*plaque-free*) and aged (*plaque-bearing*) *Tg2576 mice* J. PHARMACOL EXPT. THER. 305:864-871 (2003).

LaVail et al., PROC. NAT'L ACAD. SCI. 89:11249-11253 (1992).

Liang, J. S., Sloane, J. A., Wells, J. M., Abraham, C. R., Fine, R. E., and Sipe, J. D., *Evidence for local production of acute phase response apolipoprotein serum amyloid A in Alzheimer's disease brain*, NEUROSCI. LETT. 225:73-76 (1997).

Lin et al., CURR. EYE RES. 13(7):513-522 (1994).

Liu, Y and Schubert, D., *Cytotoxic amyloid peptides inhibit cellular 3-(4,5-dimethylthiazol-2-yl)-2,5-diphenyltetrazolium bromide (MTT) reduction by enhancing MTT formazan exocytosis*, J. NEUROCHEM. 69:2285-2293 (1997).

Marks, N. and Berg, M. J., *APP processing enzymes (secretases) as therapeutic targets: insights from the use of transgenics (Tgs) and transfected cells*, NEUROCHEM. RES. 28:1049-1062 (2003).

Matsuoka, Y. et al., *Novel therapeutic approach for the treatment of Alzheimer's disease by peripheral administration of agents with an affinity for β-amyloid*, J. NEUROSCI. 23:29-33 (2003).

Miida T., Yamada, T., Yamadera, T., Ozaki, K., Inano, K., Okada, M., *Serum amyloid A protein generates pre-beta 1 high-density lipoprotein from alpha-migrating high-density lipoprotein*, BIOCHEM. 38(51):16958-16962 (1999).

Morgan, D et al., *Aβ peptide vaccination prevents memory loss in an animal model of Alzheimer's disease*, NATURE 408:982-985 (2000).

Naash et al., INV. OPHTHALM. VIS. SCI. 37:775-782 (1996).

Nakagami, Y and Oda, T., *Glutamate exacerbates amyloid β1-42-induced impairment of long-term potentiation in rat hippocampal slices*, JPN. J. PHARMACOL. 88:223-226 (2002a).

Nakagami, Y. et al., *A novel-sheet-breaker, RS-0406, reverses β-amyloid-induced cytotoxicity and impairment of long-term potentiation in vitro*, BR. J. PHARMACOL. 137:676-682 (2002b).

Noell et al., INVEST. OPHTHALM. VIS. SCI. 5:450-472 (1966).

O'Hara, R., Murphy, E. P., Whitehead, A. S., FitzGerald, O., and Bresnihan, B., *Acute-phase serum amyloid A production by rheumatoid arthritis synovial tissue*, ARTHRITIS RES. 2:142-144 (2000).

Pike, C. J. et al., *Neurodegeneration induced by β-amyloid-peptides in vitro: the role of peptide assembly state*, J. NEUROSCI. 13:1676-1687 (1993).

Schenk, D. et al., *Immunization with amyloid-β attenuates Alzheimer's-disease-like pathology in the PDAPP mouse*, NATURE 400:173-177 (1999).

Sickenberg et al., INV. OPTHALM. VIS. SCI. 38(4):S92 (1997).

Taylor et al., ARCH. OPHTHALM. 110:99-104 (1992).

Thomas et al., INV. OPHTHALM. VIS. SCI. 39(4):S242 (1998).

Thorn, C. F. and Whitehead, A. S., *Differential glucocorticoid enhancement of the cytokine-driven transcriptional activation of the human acute phase serum amyloid A genes, SAA1 and SAA*, J. IMMUNOL. 169:399-406 (2002).

Uhlar, C. M., and Whitehead, A. S., *Serum amyloid A, the major vertebrate acute-phase reactant*, EUR. J. BIOCHEM. 265:501-523 (1999).

Urieli-Shoval, S., Cohen, P., Eisenberg, S., and Matzner, Y., *Widespread expression of serum amyloid A in histologically normal human tissue. Predominant localization to the epithelium*, J. HISTOCHEM. CYTOCHEM. 46:1377-1384 (1998).

Walder et al., *Tanis: A link between type 2 diabetes and inflammation?* DIABETES 51:1859-1866 (2002).

Xia, W., *Relationship between presenilinase and γ-secretase*, DRUG NEWS PERSPECT. 16:69-73 (2003).

Yamada et al., *Serum amyloid A secretion from monocytic leukaemia cell line THP-1 and cultured human peropheral monocytes*, SCAND. J. IMMUNOL. 52:7-12 (2000).

Yamazaki et al., BIOCHEMICAL AND BIOPHYSICAL RES. COMM., 290:1114-1122 (2002).

Young, SUR. OPHTHALM. 32:252-269 (1988).

Zhang, L. et al., *α-Lipoic acid protects rat cortical neurons against cell death induced by amyloid and hydrogen peroxide through the Akt signaling pathway*, NEUROSCI. LETT. 312:125-128 (2001).

We claim:

1. A method for treating glaucoma, said method comprising topically administering to the eye of a patient in need thereof a therapeutically effective amount of a composition comprising a Tanis antagonist, wherein said Tanis antagonist is α-lipoic acid and wherein the concentration of α-lipoic acid in said composition is from 0.01% to 5% by weight.

* * * * *

SEQUENCE LISTING

```
<160> NUMBER OF SEQ ID NOS: 17

<210> SEQ ID NO 1
<211> LENGTH: 369
<212> TYPE: DNA
<213> ORGANISM: homo sapiens

<400> SEQUENCE: 1
atgaagcttc tcacgggcct ggtttctgc tccttggtcc tgggtgtcag cagccgaagc      60 ttctttcgt tccttggcga ggcttttgat ggggctcggg acatgtggag agcctactct     120
gacatgagag aagccaatta catcggctca gacaaatact tccatgctcg ggggaactat     180
gatgctgcca aaagggacc tgggggtgtc tgggctgcag aagcgatcag cgatgccaga     240
gagaatatcc agagattctt tggccatggt gcggaggact cgctggctga tcaggctgcc     300
aatgaatggg gcaggagtgg caaagacccc aatcacttcc gacctgctgg cctgcctgag     360
aaatactga                                                            369

<210> SEQ ID NO 2
<211> LENGTH: 122
<212> TYPE: PRT
<213> ORGANISM: homo sapiens
```

<400> SEQUENCE: 2

| | | | | | | | | | | | | | | | |
|---|---|---|---|---|---|---|---|---|---|---|---|---|---|---|---|
| Met | Lys | Leu | Leu | Thr | Gly | Leu | Val | Phe | Cys | Ser | Leu | Val | Leu | Gly | Val |
| 1 | | | | 5 | | | | | 10 | | | | | 15 | |

Ser Ser Arg Ser Phe Phe Ser Phe Leu Gly Glu Ala Phe Asp Gly Ala
        20                  25                  30

Arg Asp Met Trp Arg Ala Tyr Ser Asp Met Arg Glu Ala Asn Tyr Ile
            35                  40                  45

Gly Ser Asp Lys Tyr Phe His Ala Arg Gly Asn Tyr Asp Ala Ala Lys
 50                      55                  60

Arg Gly Pro Gly Gly Val Trp Ala Ala Glu Ala Ile Ser Asp Ala Arg
65              70                  75                  80

Glu Asn Ile Gln Arg Phe Phe Gly His Gly Ala Glu Asp Ser Leu Ala
                    85                  90                  95

Asp Gln Ala Ala Asn Glu Trp Gly Arg Ser Gly Lys Asp Pro Asn His
                100                 105                 110

Phe Arg Pro Ala Gly Leu Pro Glu Lys Tyr
            115                 120

<210> SEQ ID NO 3
<211> LENGTH: 570
<212> TYPE: DNA
<213> ORGANISM: homo sapiens

<400> SEQUENCE: 3

```
agggacccgc agctcagcta cagcacagat cagcaccatg aagcttctca cgggcctggt      60
tttctgctcc ttggtcctga gtgtcagcag ccgaagcttc ttttcgttcc ttggcgaggc     120
ttttgatggg gctcgggaca tgtggagagc ctactctgac atgagagaag ccaattacat     180
cggctcagac aaatacttcc atgctcgggg gaactatgat gctgccaaaa ggggacctgg     240
gggtgcctgg gccgcagaag tgatcagcaa tgccagagag aatatccaga gactcacagg     300
ccatggtgcg gaggactcgc tggccgatca ggctgccaat aaatggggca ggagtggcag     360
agaccccaat cacttccgac tgctggcct gcctgagaaa tactgagctt cctcttcact     420
ctgctctcag gagacctggc tatgaggccc tcggggcagg gatacaaagt tagtgaggtc     480
tatgtccaga gaagctgaga tatggcatat aataggcatc taataaatgc ttaagaggtc     540
aaaaaaaaaa aaaaaaaaa aaaaaaaaa                                       570
```

<210> SEQ ID NO 4
<211> LENGTH: 122
<212> TYPE: PRT
<213> ORGANISM: homo sapiens

<400> SEQUENCE: 4

Met Lys Leu Leu Thr Gly Leu Val Phe Cys Ser Leu Val Leu Ser Val
 1               5                  10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
 50                  55                  60

Arg Gly Pro Gly Gly Ala Trp Ala Ala Glu Val Ile Ser Asn Ala Arg
65              70                  75                  80

Glu Asn Ile Gln Arg Leu Thr Gly His Gly Ala Glu Asp Ser Leu Ala
                    85                  90                  95

Asp Gln Ala Ala Asn Lys Trp Gly Arg Ser Gly Arg Asp Pro Asn His
            100                 105                 110

Phe Arg Pro Ala Gly Leu Pro Glu Lys Tyr
        115                 120

<210> SEQ ID NO 5
<211> LENGTH: 4286
<212> TYPE: DNA
<213> ORGANISM: homo sapiens

<400> SEQUENCE: 5

```
gatggttgac aactcccctc ctcttccccc tcttctactg tctactcctg ggaccaagtg      60
agccacgcca gctcagatac tacactgacc acagggaatc ccaccttttc caaggaatgg    120
aagttgtgta gggaatattc aaatgttgct tagcattgcc ttagataaga accaaaggga    180
cagggaaatc ctctgacagc tatctgcctt ataactttca ttttactgtg cctaaaatat    240
gctcagaacc cagaaagagg cataattcct aattttggca ggctctaatc taaaataatg    300
attctcaaac atggtgtgac ttttgtctat ttgctttatc ctgggtcact gctcctcttc    360
tgtcagatac tgggattcca atgagacaaa tggaaatgga gacgtagacc ctctgacctt    420
ctatctttta tctatacaca tacacctgtg tgtgtgtgtg tgtgtgtgtg tgtgcgtgtg    480
taaaaccgag tgggtttttt tcttggaatg aaagaatgga ctaacattac aaaaaataaa    540
aacttgaaac agaatgtgta ttatccttgg ttgtgtttcc ttggccctgc agcaggatga    600
agctctccac tggcatcatt ttctgctccc tggtcctggg tgtcagcagc caaggatggt    660
taacattcct caaggcagct ggccaaggtg aggtccacag gataggggc aggaggctgc     720
ttctggctgc ccccaggatg cagctgagca gaggccacat ccccactggg caaggtgct     780
agtgatgcca cagatggata gagaaggggc atggtttttc ataagcgtgg ttcctcatgc    840
ttttctggac agctttgaca ctcttctatg aggatcctcc agccgaggtc gcataaggtg    900
tgagctgcct cttttcagca ggaccatgag agagatgtgg agttgagggg tgcatgttcc    960
cataataccg gtgggctct actgcccccct agtgggaaat ctgggacagt tcatgtctat   1020
gtctcctggg aagccaggaa gcaggtggat caaaagtgtg aggcgagtcc atgggaagc    1080
tgaacggagc caaccgtccc cataaaaaca accaagctta gctgagattt taatacgtac   1140
taggcactgt ttaaatgtac taatgaattg gtttccatca tttagtccta tgatgcaagc   1200
agcattatcc cttaacagag aagctaacac acacacacac acacacacac taacacacac   1260
acacacacac acacacacac aaaccccaag atacgtaaag aagttccaaa gcagagcagg   1320
attaacccag gcagtcttgc tctgcagaac ttgctcttaa tcaaggtact ctgctgcttt   1380
caaaacaaga gtttcggatt tgtgaacaca tagctcatcc tttatctaag aaatggcaaa   1440
taggatgtgg tgcctttgga aggtaagtct agctccactt atcccagtaa aacctacagt   1500
gaattacctt gatggtggtt ctactggggc ttatatatgg ccaggaaact gctagcaaga   1560
gaaatatacc ccgagggctg gcacagtgg ctcacacctg taatcccagc actttgggag    1620
gctgaggtgg gcagatcacc tgaggtcaag agttcgagac cagcctggcc aacatggcga   1680
aatcctgtct ctactaaaaa tacagaaatt agccgggtgt ggtggcatgc gcctataatc   1740
ccagcctctc gggaggctga gggagaagaa ttgcttgaac tcaggaggca gaggttgcag   1800
tgagctgtga tcacaccact gcactccagc ctaggagaca gagcaagact ccatctagag   1860
agacagagag agagagagag ggagaaatat accccactag ccataataaa gtggcaaaat   1920
```

-continued

```
tttgttttca gaatgcagta ttttaaattt caggtattat tattttttctg agtctctgaa      1980 aaatggtttt aaggatttgc ttttaatcct atttacatgt tcacacactc aactacaaat      2040
atctttcatt ccttaggtta atattttca aagggttgtt ctgggaccac ttgcgtgaga       2100
atcacctgga ttctgggatg ctttgtgaaa tgaaatgaag attcccgggt ccataccta       2160 cccccctgccc caacagcca cagtctcttg gacagagcc tagaaatctt gcctttgcta       2220
agcacctcgg tagattttta tgcacagcaa aggttgagaa ccactacctc ttgttttgct     2280
gctgaaagtg ataaaatgtg ccaggaattt tggaagtact tattaagcca atctgaacat    2340
caaggagcca tttaagtcag taactcagag gaataagtag agtaaaaatg tcataaactc   2400
tcaataaaag caatcaattt aacaccagga gtaataaatg cataaaatga agatgagtta    2460
tctaatagag aaattatata aaccatgatt ataactctat atttgagttc cccctttttcc     2520 gtaatcagtt aattttctaa aaaatcttcg tcacttaatt ctagcttgat cagatcccctt      2580 cagtccgtaa ctccctgctc ctcatcttag tttagccctt ctttttctt atgccacctt        2640 tcctaaggac cagagaagtg aaatgataat atattggcca cctacaatgt tctagacatc    2700
atacatgtat tttctctgct cttctgcata atcactgtga ggcaggcaat actcctccat     2760
ttcattgggg aggacattga ggttctgaac tagtgggtca gttgtccttt ttctgaattt      2820
gattacccag tagtataaag cttctcttagg taactcacct ttatcacttg ctgactgaat   2880
tctgacagat gtcagtttct aattatagcc tggacattca gatgtattca ggaccaagtt    2940
gtcctcactc tacctacagg catgaatttc tctcattgac taggttagga gcgccatatg    3000
tctgcagcct ccctcagaat ccctgtgtt ctcaccag ggaactgagg gttccctggg       3060
tccttccagg tagaagttca ttgtacaatg aaacatccct taaggaccat ttcatctctt    3120
ctttaggtgc atcacacatg gttaaaacaa agtaataaca gaacttagaa tggaatcaaa   3180
cagaatgaaa cttacaccaa gtacaattct cattacatta acccagaaa gtgaaaagta     3240 gaagaatatt tatttcaagc caatataatt tccaagggct ttgttgaagg ctgaaatctt    3300
cgggaggaaa gtagtgagaa gaaaactgtt cattcctcta ttttcccagt atataattgt    3360
tttgatcatt ttctttcctt tccagggact aaagacatgt ggaaagccta ctctgacatg   3420
aaagaagcca attacaaaaa attcagacaa atacttccat gcttgggga actatgatgc    3480 tgtacaaagg gggcttgggg ctgtctgggc tacagaagtg atcaggtaat gcacattcct   3540
gatgttgcca ggaatgagtg agcagagctt gactgccttg acagtcagg agagaggtaa    3600 gctccttgca gagaagttag aggctgcagc ccctcctcct cttgccctct ctctgcctgt    3660
gtgcttagtg cgagggtctg agtggatggt agaagtgagt gattcctcac cctccctctc    3720
tgggtgctgt tcatccagcc tagggtgcc cagcctggct gagtggggca gtgcccaggc    3780
agggtcattg ttttcacccc tccttccttg gccttcctgg gcttctccca gagtcctccc    3840
ttggaaagca gagaatggga aggtgggctg ttgctcactg gcctggtgat taatctcctt    3900
gcttgcctgg actacagcga tgccagagag aacgtccaga gactcacagg agaccatgca   3960
gaggattcgc tggctggcca ggctaccaac aaatggggcc agagtggcaa agaccccaat   4020
cacttccgac ctgctggcct gccagagaaa tactgagctt ccttttcaat ctgctctcag   4080
gagacctggc tgtgagcccc tgagggcagg acatttgtt gacctacagt tactgaattc      4140
tatatcccta gtacttgata tagaacacat aaaaatgctt aataaatgct tgtgaaatcc   4200
agtttgttat tggaatctgg aagcagaata tgacagtctt cctgggatca tgggcctgtt    4260
tagtaccata gggatgacca ataaac                                        4286
```

<210> SEQ ID NO 6
<211> LENGTH: 193
<212> TYPE: DNA
<213> ORGANISM: homo sapiens

<400> SEQUENCE: 6

```
gttttctgct ccttggtcct gggtgtcagc agccgaagct tctttcgtt ccttggcgag      60
gcttttgatg gggctcggga catgtggaga gcctactctg acatgagaga agccaattac    120
atcggctcag acaaatactt ccatgctcgg gggaactatg atgctgccaa aagggacct    180
gggggtctgg gct                                                       193
```

<210> SEQ ID NO 7
<211> LENGTH: 64
<212> TYPE: PRT
<213> ORGANISM: homo sapiens

<400> SEQUENCE: 7

```
Val Phe Cys Ser Leu Val Leu Gly Val Ser Ser Arg Ser Phe Phe Ser
1               5                   10                  15

Phe Leu Gly Glu Ala Phe Asp Gly Ala Arg Asp Met Trp Arg Ala Tyr
            20                  25                  30

Ser Asp Met Arg Glu Ala Asn Tyr Ile Gly Ser Asp Lys Tyr Phe His
        35                  40                  45

Ala Arg Gly Asn Tyr Asp Ala Ala Lys Arg Gly Pro Gly Gly Leu Gly
    50                  55                  60
```

<210> SEQ ID NO 8
<211> LENGTH: 369
<212> TYPE: DNA
<213> ORGANISM: homo sapiens

<400> SEQUENCE: 8

```
atgaagcttc tcacgggcct ggttttctgc tccttggtcc tgagtgtcag cagccgaagc     60
ttctttcgt tccttggcga ggcttttgat ggggctcggg acatgtggag agcctactct    120
gacatgagag aagccaatta catcggctca gacaaatact tccatgctcg ggggaactat    180
gatgctgcca aaaggggacc tgggggtgcc tgggccgcag aagtgatcag caatgccaga    240
gagaatatcc agagactcac aggccatggt gcggaggact cgctggccga tcaggctgcc    300
aataaatggg gcaggagtgg cagagacccc aatcacttcc gacctgctgg cctgcctgag    360
aaatactga                                                            369
```

<210> SEQ ID NO 9
<211> LENGTH: 122
<212> TYPE: PRT
<213> ORGANISM: homo sapiens

<400> SEQUENCE: 9

```
Met Lys Leu Leu Thr Gly Leu Val Phe Cys Ser Leu Val Leu Ser Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60
```

```
Arg Gly Pro Gly Gly Ala Trp Ala Ala Glu Val Ile Ser Asn Ala Arg
 65                  70                  75                  80

Glu Asn Ile Gln Arg Leu Thr Gly His Gly Ala Glu Asp Ser Leu Ala
                 85                  90                  95

Asp Gln Ala Ala Asn Lys Trp Gly Arg Ser Gly Arg Asp Pro Asn His
            100                 105                 110

Phe Arg Pro Ala Gly Leu Pro Glu Lys Tyr
        115                 120
```

<210> SEQ ID NO 10
<211> LENGTH: 369
<212> TYPE: DNA
<213> ORGANISM: homo sapiens

<400> SEQUENCE: 10

```
atgaagcttc tcacgggcct ggttttctgc tccttggtcc tgagtgtcag cagccgaagc     60
ttctttcgt  tccttggcga ggcttttgat ggggctcggg acatgtggag agcctactct    120
gacatgagag aagccaatta catcggctca gacaaatact ccatgctcg ggggaactat     180
gatgctgcca aaggggacc tgggggtgcc tgggccgcag aagtgatcag caatgccaga     240
gagaatatcc agagactcac aggccgtggt gcggaggact cgctggccga tcaggctgcc    300
aataaatggg gcaggagtgg cagagacccc aatcacttcc gacctgctgg cctgcctgag    360
aaatactga                                                            369
```

<210> SEQ ID NO 11
<211> LENGTH: 122
<212> TYPE: PRT
<213> ORGANISM: homo sapiens

<400> SEQUENCE: 11

```
Met Lys Leu Leu Thr Gly Leu Val Phe Cys Ser Leu Val Leu Ser Val
 1               5                  10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
 50                  55                  60

Arg Gly Pro Gly Gly Ala Trp Ala Ala Glu Val Ile Ser Asn Ala Arg
 65                  70                  75                  80

Glu Asn Ile Gln Arg Leu Thr Gly Arg Gly Ala Glu Asp Ser Leu Ala
                 85                  90                  95

Asp Gln Ala Ala Asn Lys Trp Gly Arg Ser Gly Arg Asp Pro Asn His
            100                 105                 110

Phe Arg Pro Ala Gly Leu Pro Glu Lys Tyr
        115                 120
```

<210> SEQ ID NO 12
<211> LENGTH: 10001
<212> TYPE: DNA
<213> ORGANISM: homo sapiens

<400> SEQUENCE: 12

```
gggtggatca cgaggtcagg agatcgagac catcttggct aacatggtga accccgtctc     60
tactaaaaa  tacaaaaaaa ttagccgggc gtcatggtgg cgcctgtag tcccagctac     120
tcgggaggct gaggcaggag aatggtgtga acccgggagg cagaacttgc agtgagccta    180
```

```
gatcgcgcca ctgcactcca gcctggggga caaaacgaga ctctgtctca aaaaaaaaaa    240
aaaaaattcc cacattagag ttggggaaat gggcagtcct ggtggaagtt agggaacaga    300
tctgggacac gttatagcca gctggactac aggaggccat aagctcaatt cttccttgac    360
tctgaaacct tccactggtc ctaatgccta gtaattccag gcctttccca gttgtgccag    420
gcttggaggt gaacacatct atgtgccaag aaggaaaggt atgccaagca ggggcttaag    480
tcatccttat cctcagtctg tctatgagtg gtatgtaccc ctgttcccct tgcaagatct    540
gctgggctta ggtctcctgg ctgtgagttc cccatacctg gcataaatg tagtgagcct    600 gagctcccaa ataaggttgg gggctccaga gaggtggaga gccctgtgtc tgggaagtgt    660
gcccacccag caggtctgac caggaagata cactgctagg gttatggaaa aagactatgt    720
gtcaaggtct cttgattctc catctaggca gagaatcatc tttaattaat gggaaactgg    780
aaggcaaatt acttggacct gaaattactt tttgtttatt gaaccactgt gttgtaaatc    840
acatctctct gaaggcaaga gaaatcaggg agttacaaaa tgtttaggag aactaaacag    900
gactccctgt tttgctaact aatcagattg agacaggctc tctggtaaat ctacaaattt    960
gatgttgttc aaccataagc agtaaatttc ctatgctgga ttttcctgac aatgaatgta   1020
aaaggaaaag gagtcttttt gacaaaatat tttattgttc atctaaactg aaaaacttct   1080 ctattttttca aaattgctat acgtgtttaa agatgtagat atttgaatag cctaactggt   1140
acagaaggtt taatgatgat tcctaagaca tacctataaa ttacttgaaa ttgaaacgaa   1200
atttaagaag aattattgga attttcccct tctcaaatga gttcttagtt tcataaatac   1260
tatacaagtc cataagagat ttggggtttt gagatgtctt tttttttttt tttttttcag   1320
acggagtttc actgttgttg cctaggctgg agtgcaatgg cgtgacctca gctcactaca   1380
acctccacct cccaggttca agcgattttc ctgcctcagc ctcccaagta gctgggatta   1440
cagggacctg ccacaacgcc aagctaatgt tttgtatttt tagtagagat ggggttcacc   1500
atgttggcca ggcttgtctg gaactcctga cctcaggtga tccacccgcc tataatttat   1560
tactcccttt tgcaaatgtt tgaaaaggaa taaagtgcaa tatttttaaa cagaatgcag   1620
agttctgttg tcctttggca ataccagttt cagactctga gagtggctct tgctgttgcc   1680
gacagtgggc tgatgaccaa atcccaacat gcccccgctg cgagtccttc ataacctgat   1740
tcagtcatca cttagaggcc agcaggcttc agggaggcgt gagcctcagc caacaaccta   1800
taggggaaga gacgcagaac tcaatgcaga caggtttgga ttctggtgcc tagagaatgc   1860
aacttggaaa ctctgagcca ggagaaaagg gttctctctc catgagagag tgtgggcttt   1920
gtgagaagcg acacacagca aacacaatta agagtccacc cctcagcggg gcgcaggggc   1980
tcacgcctgt aatcccagca ctttgggagg ccgaggcggg tggatcacga ggtcaggaga   2040
tcaagaccat cctggctaac acagtgaaac cctgtctcta ctaaaaatac aaaaaaatta   2100
gccgggcgtg gtggcgggcg cctgtggtcc cagctactcg ggaggctgag gcaggagaat   2160
ggtgtgaacc cggaggtgg agcttgcagt gagccgagat cgcgccactg cactccagcc   2220
tgggcgacag agcgagactc catctcaaaa aaaaaagaa aagaaaaag aaaagagtc     2280 cgcccctgaa ttaaatagtt ggtcctttg tgttcctggt gattcacttg ctaagtggaa    2340
gaaacaggag ggaatctttt ctcctgccct cctggtaatc catagcccat ggcctggctt   2400
tacttctgta aagtggcagg agacctttg acagctgagc catttcttat tttatttatt   2460
ttaataagag atggtaggaa tgagcaatga tattagtacc tggggactgt tgttcttaag   2520
```

```
gagaaacaat cttagaatga ttagtgatac cccttgcttt ctcttttctt tcattatact   2580
ttttgtacac atattttcc catttattta ttggaatctt actgatttat tataagtata    2640
agctttatgt ctacacatgt ataatcattt ttccccaagt ataagtctct ttttcatgga   2700
ggcacagcct agacctggtt agccgccatc tcccctcatt gtatgcccaa tatctattgt   2760
agtatctgct gcatagaagg cactcgatgc gtgaatggat aatgactgat gatgaatcaa   2820
taaataaatg gacatgtcat tgtaaaaaat tctaaaaatc tagaataaca caagctgttg   2880
gcactaccta gaaacacaga tgtaaaactt cctaggttgt gtttcaccat gggaacatgt   2940
ctttgaacaa aaatgggatc atattctatt gcactctttc ccttaagaga tacttctcca   3000
ggtcattaag tgctcttcca caatatcagt atatggcaga ggcaaggtca taccaggtct   3060
gtctgaaacc agggcttggc tcttaacttg cagccatact gcctccaagt ctaggtggct   3120
gggttttagg atctgtaatg ggaactcagt gtcacaacct ctactgggaa ggtattctgg   3180
tgttgcataa caggactttc tgttagagat aaccatggca aaatgaaata gagacaaagt   3240
tcaggtttct gctgccagga gctgagattg ctgtgaccaa tggcattctc ccaaaccaaa   3300
taatccaacc tggaattacc ataaaccact cctcatcttt tcaaggggtg tccaagttcc   3360
cagaaaagaa catttgttaa gggatggagg caaggaggtg gagaagaaag agcactggcc   3420
aaggtatcat gagtgtcctg ggttctggtc cttgaataag ccatttatct tctctgcagc   3480
ttctccatct gataggagtt tggaggcaga gttttttctt aatgagcaaa agacagtcgt   3540
gcctaggaga tgtggtgtac atgttagaaa gaagggactg gctgtgactc tataaaagat   3600
gaattcatac aaaaacaaat taccctttcc cagggagaaa gtttggatcc agtaattaga   3660
gatctcaaaa agtagaagac ctgccctgtg aggcctgtgg cctccaagtt tgaatgctgt   3720
gtgtcagctt taaaaactag tttcttgctg ataaatgttt catattaagc atgtgttgag   3780
agtactcctt gcctaccttc actagccact gtttccttcc cctcctccct tgtcccttca   3840
ttctctccag aactttctgc taacttccat tctcttcagg acttcagcat ggttgggaga   3900
agatcagaaa ggcatcctca ctgttttat tttagtccac ttgacctttg gggagtagtt    3960
ccactggctc ataagtatca gccccccata gcacagcacc ccacactgag cccggaagca   4020
ataaagaatc ccaatctgct gtcactaacc agcacgctca actgccatgc cctttactct   4080
tctcatctcc ctgctttcac gtcacaccaa ctaatttctc tatgagtcag cctcaactct   4140
cccaacactc tgcccaccct tcttctacta ccttccagtg agctcctcga aagaagggtc   4200
tgcggtgagg atgccccttt atctctgcct atttccttcc cattacaaaa acttgaaacc   4260
tgcctttccc atgttgattt cactttattc tcatctttac ccatgggta tgcctcctgc     4320 aattcctcct agacaataga atgagaaaga ggggtcctcg tcctctttgc tttccatgac   4380
catttctcca ttcttcacct ctgtgatgtg tcctctttga agtccctgat aaattcatta   4440
ccaccttctc tccagtctta ctaatgttat ctgcacaagt gatttccaaa caggaagatt   4500
ttcaaacact gattcctgaa gatcaccccc aactcgctga actgagacca agacctccaa   4560
gattatggct taggaatctg catttttttt tttttttga gacaagagtc tcgctctgtt    4620
gccaggctag agtgcaatgg tggaatcata gctcattgta acctcaaact cctgggctca   4680
agtgatcttc ctgcctcagc ctcccaagta gtgaggacaa caggagtgtg ccaccatgcc   4740
cagctaattg ttaattttt gtagaaatgg agtctcacta tgttgctcgg gctggtctca    4800
aactcctgac cttaacccat cctccgcctc cgccccaaa agtgttggga ttacaggtgt    4860
gagccaccgt gcccagccta gaaataccca ctagaagctt ctgtgtagac aatctgctta   4920
```

```
gtgatgtttg gagacaaagt acctctttat tgtattcatt gacaaaactc tccagtcctc    4980
tcccatcttc atggaaaatt ttcacagttc atttacggcc ctctttccaa cacattcact    5040
gccaatactc ttattgacaa taactgtatt gttgaacctt ccagtatcct gcattcccgg    5100
atcaaggccc cctcaaagcc ctgatatgca aatatctggg aaaagaatgt tccagaggaa    5160
aggaacagct aatccgaggc ccctagggta agatgtgcct gggggtttgg agaccagtgt    5220
ggccagagca aaatgagcag gaggagagaa ttggatgatg aggtacgaga ggaaggagtt    5280
aggacagttt gagtaaagtt tgaaaaccat tataagggct ttgacttcaa ctatgagtgg    5340
aagtggaatc ctccggagag ttttgaatgg agagtgatag aagttgtctt gtgttgtaac    5400
agtctggctg ctatactgaa aagagactag ttggcggcaa aggggaaat gtggaagcca    5460 gttaagaagc catcataacc cagaaggtga tgcctaataa catctctctg ggagcagcgg    5520
agagatgata agggtttgcc ttctgaatat gttttttgac aattaatgta aacatttcaa    5580
gtaggctgag attttattgc atattaacaa tgtccatgtt cactcgcggc agccgcccccc   5640 ttctgcgcgg tcatgccgag ccagcacctg ggcctggaac tgggccgcag ccccagctt    5700 cacccaccac ctccctacca tggacccctg caaagtgaac gagcttcggg cctttgtgaa    5760
aatgtgtaag caggatccga gcgttctgca caccgaggaa atgcgcttcc tgagagagtg    5820
ggtggagagc atgggaggta agtaccacc tgctactcag aaggctaaat cagaagaaaa    5880
taccaaggaa gaaaaacctg atagtaagaa ggtggaggaa gacttaaagg cagacgaacc    5940
atcaactgag gaaagtgatc tagaaattga taaagaaggt gtgattgaac cagacactga    6000
tgctcctcaa gaaatgggag atgaaaatgt ggagataacg gaggagatga tggatcaggc    6060
aaatgataaa aaagtggctg ctattgaagt cctaaatgat ggtgaactcc agaaagccat    6120
tgacttattc acagatgcca tcaagctgaa tcctcgcttg gccattttgt atgcaaagag    6180
ggccagtgtc ttcgtcaaat tacagaagcc aaatgctgcc atccaagact gtgacagagc    6240
cattgaaata aatcctgatt cagctcagcc ttacaagtgg cggggaaag cacacagact    6300 tctaggccac tgggaagaag cagcccatga tcttgccttt gcctgtaaat tggattatga    6360
tgaagatgct agtgcaatgc tgaaagaagt tcaacctagg gcacagaaaa ttgcagaaca    6420
ttggagaaag tatgagcgaa acatgaagaa gcgagagatc aaagaaagaa tagaacgagt    6480
taagaaggct caagaagagc aggagagagc ccagagggag gaagaagcca gacgacagtc    6540
aggagctcac tatggccctt ttccaggtgg ctttcctggt ggaatgcctg gtaattttcc    6600
cggaggaatg cctggaatgg gagggacat gcctggaatg gccggaatgc tggactcaa    6660 tgaaattctt agtgatccag aggctcttgc agccatgcag gatccagaag ttatggtggc    6720
cttccaggat gtggctcaga acccagcaaa tatgtcaaaa taccagagca acccaaaggt    6780
tatgaatctc atcagtaaat tgtcagccaa atttggaggt caagcataat gcccttctga    6840
taaataaagc cctgctgaag gaaaagcaac ctagatcacc ttatggatgt cgcaataata    6900
caaaccaacg tacctctgac cttctcatca agagagctgg ggtgctttga agataatccc    6960 taccctctc ccccaaatgc agctgaagca ttttacagtg gtttgccatt agggtattca    7020
ttcagataat gttttcctac taggaattac aaacttaaaa cacttttaaa atcttcaaat    7080
atttaaaaca aatttaaagg gtctgttaat tcttatattt ttctttacta atcattgtgg    7140 attttttcctt aaattattgg gcagggaata tacttattta tggaagatta ctgctctaat    7200
ttgagtgaaa taaaagttat tagtgcgagg caaacataaa aaaaaaaagt ccatgttcat    7260
```

```
ctctaaatga catcattgtt ccaaagcttt tccattcttc ttaaccttcc acctgtcaat    7320
ctataggaga tgacttctcc tacttcactc atgcattgac tccttcaatc aataaaagtg    7380
actaagaacc tgctacaggt gaggtgctgt gtttggtgtt aaagtgacaa cagttatctg    7440
tcaataagcc tgacaaggtt cctatccctg tgttttgtgc actctgggtc aaactcagaa    7500
atgcaaacag gtggagagcg atgagttcta tgactggtaa agaaaagggc ctgctggttt    7560
ccctcaggat ctctgtcctt catctcaaaa tgcatcttcc ttgttatcgt tcctctcctt    7620
cctgtctcag aggaagacct gctcctgcta cactctgggc aaccttgtcc ccgtggccct    7680
gtggcccctt ggttgttgaa gtctatgtta tgccctatct tttaccctca gtcactctct    7740
ctgttaacat tctccctgtg ccctgtaacc ctccctcatc tttaaataaa tcctcctcct    7800
ttgaccttcg catgtattca gtcatgcaac tcaacaagca tttattgcac agtgatattc    7860
aatttgccac ttgctaaaag tctgaacctt ggcagctgaa tgtgatcaga aaaaagcac     7920
gactgctatg actagtctca ctttaaattc atggtcgttg accaagagct accatacaat    7980
ccactacctt tctcaagttc agtcacattc ttccttccct agatgtctgc tttctacttc    8040
tcttctcttc tgaaacttcc cacaactcct cgttcattct cttctcagtt gacaactttg    8100
cttcctattt cactgaaaaa tagaagcaat cagatatgaa cttctggctg gcatggtag     8160
ctcatgccta taatctcagc actttgggag gccaaggcag gaggactgca ggttaggaat    8220
ttgagaccag cctgggcaac atggtgaaac tcccactgta ctaaaatttt aaaaattac    8280
tcaaacatat tggcaaacaa ctgcagtccc agctacttgg gaggttgaga tgcaaggatc   8340
acttaaacct gggaggctga ggctgcagtg agccatgatt gcaccactgc actccagctc    8400
aggcaacaga gcaagaccct gtcttgagag gagaggagaa gagaggaggg gaggggaggg    8460
caggggaggg gaggggaggg gaagggagag gggaggggag aggggaggag agaggggagg    8520
ggaggggagg ggaggggagg ggaggagagg aggatcaggt gaggagtatg ccaaggagtg    8580
tttttaagac ttactgtttt ctctttccca acaagattgt catttccttt aaaaagtagt    8640
tatcctgagg cctatattca tagcattctg aaagaaagaa aagaaaagag gaaagaaaga    8700
gagaggaagg aaggaaggag aaagagagag gaaggaagga gaaagagaga ggaaggaagg    8760
gaggaagaga agaagggagg aagaaaagaa ggaaggaagg agggagggag ggaagggagg    8820
gagggaaaga ggaagaaagg agggaaagaa ggaaggaaga gagagaggaa ggaaggagga    8880
agagagaaga aggaaggagg aagacagaga gggagtaagg aaggaaggaa ggagaaaagag   8940
agaggaagga agaaatgaag gaaggaagga aagaaagaaa aataaaaga gtgaaaacgg     9000
actggagaag aagaaaccac agttgctgct atatccacca gcctctctgc atgtcctggc    9060
ctcagccctg ctgggctctg gtactgacca cttccttcct tcctaatttc ctaattgact    9120
aggccagctg agcagggctt ttctgtgctg aggaggtaaa tctctggata tctagactga    9180
ggggtggaag gagccttcca gggcacacat gagacatggc aggggtaggc tgctagtttt    9240
attttgtttt cttttagaca cagggtcttg ctctgttaac caggctggag tgcagtggcg    9300
tgattatagc tcactgcagc cttgacctcc tgggtctccc acaatccttc cgcttcagcc    9360
tcttgagtag ctgggactgc aggtgcacac taccacaccc ggtccattta tttttatatt    9420
tcgtagagac aagatcttac agttttgcac agagtgatct taaactcttg accccaagtg    9480
atcctcctgc cttggcctcc aaaagcattg ggattatagg agtgagccac tgtgctggac    9540
ctagtctgtc agctttgaag ctttagatat gaactcagag ggacttcatt tcagaggcat    9600
ctgccatgtg gcccagcaga gcccatcctg aggaaatgac tggtagagtc aggagctggc    9660
```

```
ttcaaagctg ccctcacttc acaccttcca gcagcccagg tgccgccatc acggggctcc     9720
cactctcaac tccgcagcct cagcccctc aatgctgagg agcagagctg gtctcctgcc      9780
ctgacagctg ccaggcacat cttgttccct caggttgcac aactgggata aatgacccgg    9840
gatgaagaaa ccactggcat ccaggaactt gtcttagacc gttttgtagg ggaaatgacc    9900
tgcagggact ttccccaggg accacatcca gcttttcttc gctcccaaga aaccagcagg    9960
gaaggctcag tataaatagc agccaccgct ccctggcagg c                       10001

<210> SEQ ID NO 13
<211> LENGTH: 10001
<212> TYPE: DNA
<213> ORGANISM: homo sapiens

<400> SEQUENCE: 13
gtctgccagg gagaggtggc tgctatttat agtgagcctt gctggtctct tgggagggaa      60
gaaaagctgg atgtggtccc tggggaaagt ccctgcaggt catttcccct acaaactggt     120
ctaagacaag ttcctggatg ccggtggttt cttcatcccg ggtcatttat cccagttgtg     180
taacctatgg gaacaagaga ggtttgctgt gccttggcaa tggacagggt gctagatcag     240
ctctgctcct cagcattggg ggaagtgcag ctgcagagat gccagtggga gccccgtgat     300
ggcggcacct gggctgctgg aaggtgtgga gtgagggcag ctcttcagcc agctcctgac     360
tataccggtc atttcctcag gatgggccct gctgggccac atggcagatg acctgactg      420 aaatccctgt gagttcatgt ctaaagcttt aagctttaaa acggacagcc taccctgcc      480 acatctcatg tgtgccctgg aagcctcctt ccaccctct ggatgtcctg atatttctca     540
gcacagaaaa tctctgctcc gctggcttag ccaatttgga aatgcttttt ctaagttggc     600
tcctgagcca aggacaatgt agagaggggg actttctgct gccccagcct agtcctggag    660
ccccaccttg ggagaatgag agtgtggtgc gttaaatagg cagcccagct ggggacgtgc     720
ccagcatcca ggcagggaag ggtgggagag ctcttggtct gctgtattat cacggagggg    780
tgcagggggc atgcagatca ctctctcatg agaacatcaa caggggtcaga ttagctctgc   840 agaggcttat ggaggagcat ggtggccaga gatgggtcag taccagagcc cagggggggct  900 gaggccagga catgcagaga ggctggtgga catagcagca actctggttt cttcttctcc    960
agtccatgtt catacccctga gggctaggca tttgtaataa caaacaaaca agcaatttag  1020
aaatgggcca gcatggtgg catgtgccta tagtcccagc tacttgggag gccaaggcag    1080
gaggcctgct tgaacccaga aatttgaggc cagcctgggc aacacagcaa gattatctta   1140
aaaaattttt tttaatctct gagaaatggg tagggccagg aagtaaagga tggccaaata   1200
ctccataagc agcaaatgcg tggctccaat gtgaacaatg atattataga ctctgttctg    1260
agacctatgc attgacacct ccacctcccc cactacatct tgccaccttaa aaaccactga   1320 gagtggtacc tgctggaatg ggtccacaca cacagtcaca catatttag gcagggtagt    1380 tgacatcccc agggaaaaag agctcacaga gagaggctga atgtttccaa ctgggtagca   1440
gtaatagtac atcatgctgt acatggtaca gcacagatca ggtgaaaata atagcacatc   1500
gtgattaacc agggcttatt ccagggagtc aagaagagtt tcatatcaga aaatctatc    1560 tttgtaattc actataccag taatcaaaga aaaggattgt acatttattt tactagatgc    1620
agaaaatgaa tttcataatt gtcaacatct actgatgata aggaaaatgt ataacaaaat    1680
aaagagacca tttctgactt gagaaaggat aaataccaat atgttatagc aacagttctc    1740
```

```
aaactgttttt ccagggaacc ctaagaatcc ctccttaggg aggctttgat ctcaaaatta    1800 ttttagaat  agtgctaaca cactatttc  atgtttcagt ctcattttct catgagtaca    1860
cacaatatga caagttagtt gatatgagtg tggatttcca catggtaact gacttttcag    1920
aagctaccac ttgttgagtt tggtataata tagaatagcc acaattatct aaaaatacca    1980
ttaaaataca ctccccatt  tcaactatat atctgtgtga ggctgaattt tcttcatata    2040
ctccaaccta aataacatat aaaacaggt  tggatgatga atcagatagg aaaatccagc    2100
tatgaaaaaa aaatcagaca tgaaaattt  tcaaagggt  aaaaccatag tactcttctt    2160 acttttttc  ttttggaaga tggttatttt tcataaaaat atattattta tgttaacata    2220
tagaagatgg ataatttttt gaagaattga taaatgttta aatttttct  ttctattatg    2280 gtaaatactg atgaatagag tccccataaa taaagttct  tgggtatt   caataatttt    2340 taatagtgta atgggatcct gagaccaaaa ggtttgagaa tcattgctct acagcaaaca    2400
ttatgtgtaa ttaagacact tcaggtgcat tctcaagaag accaataaag aggccacaat    2460
ggcaggcgtg gtggctcaca cttgtaatcc aagaacttag agaggacgag gcaggtggat    2520
cactggaggt caggaattct caaccagcct ggccaacatg gtgaaaccct gtctctacta    2580
aaagtacaaa aattagtcgg gtgtagtggc aggtacctgt aatcccaagt acttgggggg    2640
ttgaggcagg agaatcactt gaagccggga ggtggaggct gcagtgagcc gagatcgtgc    2700
cactgcactc cagcctgggc aacggagtga gacttcatca tggaaaaaaa aacaaagagg    2760
ccaggatgtc tggttgttac tgccactgtt tcacatatcc ctgaaggacc tgcccaatgc    2820
taaagaaaca caaggaaggt aagaggtgaa agagaagaaa tgaaactatc attgtttgaa    2880
gatgacacca tctttacat  agaaaacctg ttagaatcaa atggcaagct attagaacta    2940
ctaagagaat tcagtgaggc tgctgtattc atggcaaaat tttaacaatt gatagcattt    3000
ctctgcaaca ttccttaata gttataaaat acagcacaaa gtagtaccaa aaatattaac    3060
tatctaggaa ataacctctt acagagaaaa tttagtctgt taaggataaa acagtggcaa    3120
tgtacgtcat gtccacagag attatattt  agcttagcaa agataccaat tctcccaaat    3180
ttatttataa attaaatgca atgtgaatca aaatttccca ctggaatttt tatcaggaag    3240
gcaacaaatt ctttctttct ttctttcttt cttttcttat ttatttattt atttatttat    3300
ttatttattt ccttccttcc ttccttcctt ccttccttcc tttctttctt tctttctttc    3360
tttctttctt tctttctctc tctctttctc tctcccccc  tctctctctc tctgtctctc    3420
tctctctctc tttctttctt tctttctttc tttcttttta agacaaagtc tggctctgtc    3480
acccaggctg cagtgcagtg atacaatctc agctcactga aacctcaacc tctccggcat    3540
caggtgaacc tcccacctca gcccccgag  tagctgggac tacaggtgca caccactggg    3600
cctagataac tttttgtatt tattgtaaat aaacacaaaa aataaatatt ttgctcaggt    3660
tggtctggaa ctcctgggct caagcaatcc gcctgccttg gcctcccaaa gtgctagaat    3720
tacagttgtg agccaccaca cccagccaat aaattaattc tttatgatga ataagttatc    3780
tatgaaaatt aagtcagctg ggtgcggtgg ctcacgcctg taatcccagc actttgccgg    3840
gctgaagcag gtggatcacc tgaggttggg agttcaagac cagccggacc aacatagaga    3900
aaacccgtct ctactaaaaa tgcaaaatta gctgggtgtg gtggcatatg cctgtaatcc    3960
cagatactta ggaggctgag gcaggagaat tgcttgaacc cgggcggtgg aggttgcggt    4020
gagccaagat tgcaccattg cactccagcc tgggccacaa gagcgaaact ccatctcaaa    4080
aaaaaaaaaa gagaagttaa gtcaatgaaa agttaagtca attaaaaaag taagagctgt    4140
```

```
agtgtttaga tatatacaca cacacatata tatatatttta tctttatata tgtatatata   4200
tcttttcctt tttttgagac cgagtctgtt tttgttgccc aggctggaat gcagtggcgc   4260
gatctctgct tactgcaacc tctgcctccc aggttcaagc gattctcgtg cctcagcctc   4320
ccgagtagct gggattacag gtgcctgccc ccatgcccgg ctaattttttg cattttttagt  4380
agagacgggg tttcaccatg ttggccaggc tggtctcaaa ctcctgacct caggtgatcc   4440
accggcctca gcctcccaaa gtgctgggat tacaggtgtg agccaccgcg cccagccata   4500
tattttgctt ttcatctgca gctcctggat cctaactcct tgttatattg ttgggcactt   4560
taggcctcag taaacagaat ctctgtctat gaccttctcc tgtccttctt ccacctgccc   4620
aaagcaggac tctaatttga ttgtgggtca aaagactctc attccagaaa gggccttgcc   4680
tcatacccta gaggaaggaa tgctgcacag aaacgccaag tctgaacaga caagccttgc   4740
tgggtttata ccatatgctt tttgtccaat cacatttctt catggttgcc aatcatgcct   4800
atgtaatgaa gcctccataa gaacccagaa ggacagggtt cagagagttt ccacatagct   4860
gaacactatc tggagagtga acacttccta gagagtggca cacccagaga gatcatgaaa   4920
gctccacgcc cctttcccct tacctcgccc tccacatctc ttcatctgta tctttcataa   4980
tatcctttat aaataaacca gcaaatgtgt ttccctgagt tatgtgagtc actctagcaa   5040
attaatcgaa cccaaagagg gggtcatggg aaccccaact tgaagccagt cagtcagaag   5100
ttccagaggc ccagacttgc aactggggag aaagaggggg aggtcttggg gactgagccc   5160
ccaacctgtg ggatctgaca ctgtctccag gtaggtagtg ttggaactgc attggaggac   5220
actcctggtg tctgctgctt ggtgtgtggg gggaaaaacc cacacctttg gttacggagg   5280
tcttctgtgt tgacgatcat tgctgtttga gggcagaggg aatacacggt ttgagagagt   5340
tttttccctga catgagcgaa caggggacat gtactggtct ctgagatggg ggatcatggg   5400
atctgccaca gtgggggaga ccactgtgac ccctgccaca gtctttgggg cagagggtgt   5460
ctcggggggca gaagaagcga gagttgtttg cagtagcagt tatgtccaaa gtgggcgcca   5520
ggaaagtagg gctgcccagc tttgaagagc ctccttactc ccagcctgaa tgaaaccatt   5580
tcctgtaaag cgctaagcat aaagtttgcc aatggtgatc cacggagaag tgagtgtacc   5640
ccaccccgcc atcccacagg gaatgtcgga gtgatgttga tctgcaccta gggaaggaat   5700
ggttcatgag atgtggtgga gatgctgagg gcccgtggac atcagatcct accctacctg   5760
tgccaggaca agccatgcgc atgtgcttca gaccaccagg caacaggagt gttgcatgag   5820
gtgtgaagca ggcacctggg aaagaggagt gtgaacagca gatgggacac actggggggca  5880
gtcataggaa tgaaatgtcc caggatggat gcaggcaggt tatggaggac ttagtgagga   5940
ctgctctcct ggtgggaatt gtggagtggg agactggatg gagactggag gtgtttttaag  6000
tagggaagcc aacttgcaag ggtgaccagg gaaactatgt cggccaaggg tgagacatgc   6060
actggcaaga ctctcagaca gcctggctta tctaagcaga atgcttgagc catgccaacg   6120
gtgcctcgca agttgtatta atcatgtcct ttcattttgt gttttttggtg cttggcatct  6180
gggcccttgc tgaccctaag ggaccatttc tctcagagct agtcaagtcc tagacacagt   6240
aaatgactct cctgggagca tgccttccat gtgcagacca accaatcaag gtccacact    6300
cccacccacc tcctttatcg agctctcaca tcctggggca ccatccacct gcctaatca    6360
ctcaaggacc acgtcccaaa caactaggga cagcctccat gccctgcac ccattgaaat    6420
tattcatgct agccaatcct aaacctgtgt atgctgccac accattcctt cctgcagaaa   6480
```

```
cacagtaagg actcttccta caccteccct acttcctctg ctccctgact tacccactta    6540
cttcctggtg cagtcccctg tggcatagtt cactctcttc ttttgggaac tgtgaggcta    6600
tcttctcaat ggcagtcatc tcctgagctg ttggccttgc catacctaac taataataaa    6660
atctatattc taaggtaaaa acaaaacaga tagggtctca ctctgttgcc caggctggag    6720
tacagtggtg tgatcatgac tcactgcagc ctcaaactcc tgggctcaag cagttctctc    6780
atctcaacct cccgagtagc tgggactaca ggcacacacc accatgcctg gctagttttc    6840
ttattttttt tgtagataca gggtcttgtt atgttgccaa ggctggtctt gaactcctgg    6900
gctcaagtga tcctcctgcc ttggcctccc aaactgctgc aattacaggc atgagccacc    6960
atgcccagat cagaaatctt actaaaaata tttcaaggag aagagaaagc caaagatgtt    7020
gaatatatat atatgtgtgt gtgtgtgtgt gtatatatat gtatatatgt gtatatatgt    7080
gtgtatatat atatgtatat atgtatatat atatgtatat atgtatatat atatgtatat    7140
tggggcaggc gtggtggctc atgcctgtgg tcctaactac ttgagagtct gaggtgggag    7200
gattgcttga gcctgggaga tcgaggctgc tgtgagctga gactacacca ctgcactcca    7260
gcttgggtga cagagtgaga ccctgtctcc aaaaaacaa aagaaaaag aaaaaaagat     7320 ggaaaagac atgaaaaaac aacaacagaa atacccacac atcatcaatg ggagggaagc    7380
atcttgaggc agcaaagcgg gagtgctagt agagaggcag atagggcgtt ggacctgagg    7440
cattaaggaa agtcaggatt tggagcttac aagtctctca ttggagatgg gatggggttg    7500
gaatgaatgt ctgagcaaac acaaagcatt tccttcccta atgactcccc accagtctaa    7560
agaatcccac attaggtcga cacggtggc tcacgcctgt aatcccagca ctttgggagg    7620
ccaaggcggg tggatcacga ggtcaggaga tcgagaccat cttggctaac atggtgaaac    7680
cccgtctcta ctaaaaatac aaaaaaatta gccgggcgtc atggtgggcg cctgtagtcc    7740
cagctactcg ggaggctgag gcaggagaat ggtgtgaacc cgggaggcag aacttgcagt    7800
gagcctagat cgcgccactg cactccagcc tgggggacaa acgagactc tgtctcaaaa     7860 aaaaaaaaaa aaattcccac attagagttg gggaaatggg cagtcctggt ggaagttagg    7920
gaacagatct gggacacgtt atagccagct ggactacagg aggccataag ctcaattctt    7980
ccttgactct gaaaccttcc actggtccta atgcctagta attccaggcc tttcccagtt    8040
gtgccaggct tggaggtgaa cacatctatg tgccaagaag gaaaggtatg ccaagcaggg    8100
gcttaagtca tccttatcct cagtctgtct atgagtggta tgtaccctg ttcccttgc     8160 aagatctgct gggcttaggt ctcctggctg tgagttcccc atacctgggc ataaatgtag    8220
tgagcctgag ctcccaaata aggttggggg ctccagagag gtggagagcc ctgtgtctgg    8280
gaagtgtgcc cacccagcag gtctgaccag gaagatacac tgctagggtt atggaaaaag    8340
actatgtgtc aaggtctctt gattctccat ctaggcagag aatcatcttt aattaatggg    8400
aaactggaag gcaaattact tggacctgaa attactttt gtttattgaa ccactgtgtt     8460
gtaaatcaca tctctctgaa ggcaagagaa atcagggagt tacaaaatgt ttaggagaac    8520
taaacaggac tccctgtttt gctaactaat cagattgaga caggctctct ggtaaatcta    8580
caaatttgat gttgttcaac cataagcagt aaatttccta tgctggattt tcctgacaat    8640
gaatgtaaaa ggaaaaggag tcttttttgac aaaaatattt attgttcatc taaactgaaa    8700
aacttctcta ttttcaaaa ttgctatacg tgtttaaaga tgtagatatt tgaatagcct     8760
aactggtaca gaaggtttaa tgatgattcc taagacatac ctataaatta cttgaaattg    8820
aaacgaaatt taagaagaat tattggaatt ttccccttct caaatgagtt cttagtttca    8880
```

```
taaatactat acaagtccat aagagatttg gggttttgag atgtcttttt tttttttttt    8940
ttttcagacg gagtttcact gttgttgcct aggctggagt gcaatggcgt gacctcagct    9000
cactacaacc tccacctccc aggttcaagc gattttcctg cctcagcctc ccaagtagct    9060
gggattacag gacctgcca caacgccaag ctaatgtttt gtattttag tagagatggg      9120 gttcaccatg ttggccaggc ttgtctggaa ctcctgacct caggtgatcc acccgcctat    9180
aatttattac tccctttgc aaatgtttga aaaggaataa agtgcaatat ttttaaacag     9240
aatgcagagt tctgttgtcc tttggcaata ccagtttcag actctgagag tggctcttgc    9300
tgttgccgac agtgggctga tgaccaaatc ccaacatgcc cccgctgcga gtccttcata    9360
acctgattca gtcatcactt agaggccagc aggcttcagg gaggcgtgag cctcagccaa    9420
caacctatag gggaagagac gcagaactca atgcagacag gtttggattc tggtgcctag    9480
agaatgcaac ttggaaactc tgagccagga gaaaagggtt ctctctccat gagagagtgt    9540
gggctttgtg agaagcgaca cacagcaaac acaattaaga gtccacccct cagcggggcg    9600
caggggctca cgcctgtaat cccagcactt tgggaggccg aggcgggtgg atcacgaggt    9660
caggagatca agaccatcct ggctaacaca gtgaaaccct gtctctacta aaaatacaaa    9720
aaaattagcc gggcgtggtg gcgggcgcct gtggtcccag ctactcggga ggctgaggca    9780
ggagaatggt gtgaacccgg gaggtggagc ttgcagtgag ccgagatcgc gccactgcac    9840
tccagcctgg gcgacagagc gagactccat ctcaaaaaaa aaaagaaaaa gaaaagaaa    9900 aagagtccgc ccctgaatta aatagttggt ccttttgtgt tcctggtgat tcacttgcta    9960
agtggaagaa acaggaggga atcttttctc ctgccctcct g                        10001

<210> SEQ ID NO 14
<211> LENGTH: 1209
<212> TYPE: DNA
<213> ORGANISM: homo sapiens

<400> SEQUENCE: 14
cagggctggg cggcggcggc ggcggcggtc atggaacgcc aagaggagtc tctgtccgcg      60
cggccggccc tggagaccga ggggctgcgc ttcctgcaca ccacggtggg ctccctgctg     120
gccacctatg ctggtacat cgtcttcagc tgcatccttc tctacgtggt cttcagaag       180 ctttccgccc ggctaagagc cttgaggcag aggcagctgg accgagctgc ggctgctgtg     240
gaacctgatg ttgttgttaa acgacaagaa gctttagcag ctgctcgact gaaaatgcaa     300
gaagaactaa atgcgcaagt tgaaaagcat aaggaaaaac tgaaacaact tgaagaagaa     360 aaaggagac agaagattga atgtgggac agcatgcaag aaggaaaaag ttacaaagga      420
aatgcaaaga gccccagga ggaagacagt cctgggcctt ccacttcatc tgtcctgaaa     480
cggaaatcgg acagaaagcc tttgcgggga ggaggttata acccgttgtc tggtgaagga    540
ggcggacttg ctcctggaga cctggacgca gaggcccgtc atctggcgga tgaggctaag    600
aatcttgtta gtgtcacttt tgacattagc aagatgaacc cttaaccctc gattcaattg    660
ccttacgcac gcttttcaca gtgactagcc aaggggaggt ggggttgatt tctgttccta    720 actcacctg catatgtcag ggctccagtc agcaaaaggt atagatgttg cctctaggca    780
tgaggtcatt ggtcacattc tacttggaga cagtgattgc attcattgat tcatggtta    840 attgctagtt ggtaggtaaa ggcctctaga tgattagcaa tcttgataaa agaggcctag    900
taatgttctt tgaggttag aaatccttgc tgctaggaca gtctctgtga caggttgcgt    960
```

```
tgaatgatgt cttccttatc aatggtgagc ccaccagtga ggattactga tgtggacagt      1020
tgatggggtt tgtttctgta tatttatttt tatgtacaga actttgtaaa aacgaaacta      1080
tttaaaaaac aagaataaca tttttagcat ctttattcaa ggagatttat ggacttcaat      1140
ttgtctatca aacattaaat agcttttat tacaacctcc aaaaaaaaaa aaaaaaaaaa       1200
aaaaaaaaa                                                              1209

<210> SEQ ID NO 15
<211> LENGTH: 204
<212> TYPE: PRT
<213> ORGANISM: homo sapiens

<400> SEQUENCE: 15

Met Glu Arg Gln Glu Glu Ser Leu Ser Ala Arg Pro Ala Leu Glu Thr
1               5                   10                  15

Glu Gly Leu Arg Phe Leu His Thr Thr Val Gly Ser Leu Leu Ala Thr
            20                  25                  30

Tyr Gly Trp Tyr Ile Val Phe Ser Cys Ile Leu Leu Tyr Val Val Phe
        35                  40                  45

Gln Lys Leu Ser Ala Arg Leu Arg Ala Leu Arg Gln Arg Gln Leu Asp
    50                  55                  60

Arg Ala Ala Ala Val Glu Pro Asp Val Val Lys Arg Gln Glu
65                  70                  75                  80

Ala Leu Ala Ala Ala Arg Leu Lys Met Gln Glu Glu Leu Asn Ala Gln
                85                  90                  95

Val Glu Lys His Lys Glu Lys Leu Lys Gln Leu Glu Glu Lys Arg
            100                 105                 110

Arg Gln Lys Ile Glu Met Trp Asp Ser Met Gln Glu Gly Lys Ser Tyr
        115                 120                 125

Lys Gly Asn Ala Lys Lys Pro Gln Glu Glu Asp Ser Pro Gly Pro Ser
    130                 135                 140

Thr Ser Ser Val Leu Lys Arg Lys Ser Asp Arg Lys Pro Leu Arg Gly
145                 150                 155                 160

Gly Gly Tyr Asn Pro Leu Ser Gly Glu Gly Gly Leu Ala Pro Gly
                165                 170                 175

Asp Leu Asp Ala Glu Ala Arg His Leu Ala Asp Glu Ala Lys Asn Leu
            180                 185                 190

Val Ser Val Thr Phe Asp Ile Ser Lys Met Asn Pro
        195                 200

<210> SEQ ID NO 16
<211> LENGTH: 10907
<212> TYPE: DNA
<213> ORGANISM: homo sapiens

<400> SEQUENCE: 16
tgagcagcct gagatgtcag taattgtagc tgctccaagc ctgggttctg tttttagtg         60 ggatttctgt tcagatgaac aatccatcct ctgcaatttt ttaaaagcaa aactgcaat        120 gtttcaggca cagaaaggag gcaaaggtga agtccagggg aggtcagggg tgtgaggtag       180
atgggagcgg atagacacat cactcatttc tgtgtctgtc agaagaacca gtagacactt       240
ccagaattgt ccttttattta tgtcatctcc ataaaccatc tgcaaatgag ggttatttgg      300
catttttgtc attttggagc cacagaaata aaggatgaca agcagagagc ccgggcagg       360 aggcaaaagt cctgtgttcc aactatagtc atttctttgc tgcatgatct gagttaggtc       420
```

```
accagacttc tctgagcccc agtttcccca gcagtgtata cgggctatgt ggggagtatt    480
caggagacag acaactcact cgtcaaatcc tccccttcct ggccaacaaa gctgctgcaa    540
ccacagggat ttcttctgtt caggtgagtg tagggtgtag ggagattggt tcaatgtcca    600
attcttctgt ttccctggag atcaggttgc cctttttggt tagtctctcc aattccctcc    660
ttcccggaag catgtgacaa tcaacaactt tgtatactta agttcagtgg acctcaattt    720
cctcatctgt gaaataaacg ggactgaaaa atcattctgg cctcaagatg ctttgttggg    780
gtgtctaggt gctccaggtg cttctggag aggtgaccta gtgagggatc agtgggaata     840
gaggtgatat tgtggggctt ttctggaaat tgcagagagg tgcatcgttt ttataattta    900
tgaattttta tgtattaatg tcatcctcct gatcttttca gctgcattgg gtaaatcctt    960
gcctgccaga gtgggtcagc ggtgagccag aaagggggct cattctaaca gtgctgtgtc   1020
ctcctggaga gtgccaactc attctccaag taaaaaaagc cagatttgtg gctcacttcg   1080
tggggaaatg tgtccagcgc accaacgcag gcgaggact ggggggaggag gaagtgccc    1140
tcctgcagca cgcgaggttc cggaccggc tggcctgctg gaactcggcc aggctcagct    1200
ggctcggcgc tgggcagcca ggagcctggg ccccggggag ggcggtcccg ggcggcgcgg   1260
tgggccgagc gcgggtcccg cctccttgag gcgggcccgg gcggggcggt tgtatatcag   1320
ggccgcgctg agctgcgcca gctgaggtgt gagcagctgc cgaagtcagt tccttgtgga   1380
gccggagctg ggcgcggatt cgccgaggca ccgaggcact cagaggaggt gagagagcgg   1440
cggcagacaa caggggaccc cgggccggcg cccagagcc gagccaagcg tgcccgcgtg    1500
tgtccctgcg tgtccgcgag gatgcgtgtt cgcgggtgtg tgctgcgttc acaggtgttt   1560
ctgcggcagg tgaatgacgg gcgtgggtcg gtgcgcgctc ggcttgcgca cacggtgtct   1620
ctataagtgc gcgggtgacg agagtcggga tgtgccggag acccccggggc ggagagcggg  1680
attacaagta caggaatccc tggtcacgct ccccgcccct ggaaacccag ctggggcgag   1740
ggagggcgtg gacgggaccg ttctgggagc tcgccctttgg ctgcggttgg ctccaggccc   1800
caggcgcagt ttgctcgcgg cgtggggatg aagtccgtgt ccctggaggg gcccaggaag   1860
ggcgaggaaa gcggagtgga gtaagttcgt ctaggatcgg tcccgggtgg ctctgggatc   1920
caatctgcgc cgcccctggcc caggtcccag gttcaggtcc tttacgccac tgtgtccacc   1980
acctggctga gcgctgaggt cagcgcgggc tgtttcctgg cccttgggaa tgtgccagga   2040
cccgtcccct aaggactagc gaggaggtga ctcactgtga caaggagacc ccagggaacg   2100
gactgtatga ggtcagaacc ccgccgggga tggggtacag cgggactcca gaagccctct   2160
cccctgcccc ttcgcggtct ccgtcctccc atcggcacag tgacctattt ggctggaaca   2220
gtttgttccc aaggaagccg ggcactggag gtccgggaca ccgcgtcggg tccccgctcc   2280
gcggcgcgct gtaggggtcg gggagtcacg gccctgcgct gggcgggctc taaccagcct   2340
gtcagtcggg gaagggcaag ggtctcctct acctctttcc caccgcggcc gggagaatcg   2400
cggcccagcc tgtcctcggg tcgggcgct ggactccggg gcgggagcgg agcccacgcc    2460
tggatgggag gcgggaggg ttcatgtctt tgaggggtgg ggggtctggg gggcacgacg    2520
ctgctcaggg cctctatcag ctgcctcggg ggctcagggc ttcccgacct agcccagatt   2580
ccctctccga aagctacagg gctgagcgga cagggggggc gagtcgcccc ctggggcgcc   2640
gccgcctggc gcggaccaca gcgcgtcctc tccgtcccaa accctggggg acacttgcg    2700
ccctcttcgt gaggaaaagc atcttggagc tgggttagga acttgggcg cccaggcagc    2760
ttcccctctc cttgcctccc tccacgtcgc gtttctggga ggacttgcga gcggttttgt   2820
```

```
tttcgttgct cccgtctatt tttatttttcc agggatctga ctcatcccgt gctttgggcg    2880
tggagataag gtggagggc cggctcccgg cgcgcgcgcg cgtgcgtgtc tgcgcgggcg      2940
tgtgtgtgtg tgtgtgtgtg tgtgtgtgtg tgtgtgtctg tgtcagagac ggcacaagag    3000
cgcgcggttt cccaacagcg gcgggagttt cggaagcctg gccggctcag cgtgacgtgt    3060
tcgcggcccc ccgtcccct cccattctcc cctccccac cccagggtga cgcgcagccg      3120
gagtggaagc agagttttgg cgggcgagca gcgccttgca ggaaactgac tcatcactac    3180
tccctccagc ggtccgaggc tctgcccacg cacctcccac tccgcgcgtg atttcctgga    3240
ggccggcgcc ccctcccggc cctggcggga atagcacaca ggctttcccg cggagtgggg    3300
ctggccggcg cgaaccgccg cggctactcc tgggctcatc cgagatcaac ccctatgcca    3360
ttaccacccc ttcaaaggag cactccttag gttcaacagt attcactgag ctcttactgg    3420
aaattaaaat atggctgaag tctaaggcag gaaggccaat aaaggaggct attttttaatt   3480 gtttctaaaa caagggtttg cgtttctgag ttttctttgg gctgaaagtt attatgagca    3540
tgagagcaga ttttgatggg ggaggagagg cctatgagag ccataagaga aggagggtg     3600 gtagaagagg agagggtgcc tgcctagatc ctagtcctgt cttgaactcc cgagagccag    3660
ggaatatcca gctccttgat gaagcccctag gcgggcgcct cctccttgtg cctatgatgt   3720
attgagaccc agaatgtcca tttcaaacat accagtgtgt ctccgcttgg ctggcacccc    3780
aagagtgccc atctgaggaa ttgtgccaaa cacttgcttg aatcttcaat ttggattaag    3840
ttggtctcgg gaggcagggc ctcagcaatc tatattttga aaaaactccc taggtgcttt    3900
tctttctttc tttctttctt tctttctttc tttctttctt tctttcttc tttctttctt     3960 tctttctttt tctttctttc tttctttttc tttctttct ttcttcttt ctttctttct     4020 ttctttcttt ctttctttct tcctttctct ttctctcttt cttttctctt ctctctttct   4080
ttcttttctt tcgacagagt tgcactctgt cacccaggct ggagtgcaat ggcaccatcc    4140
tggactcaag tagtcctcct gtttcagcct cccaagtaac cgggaccaca ggcgtgatcc    4200
ccccgccccc atgcccagat ttttttttt ttttttttt ttttgagatg cggtctcgct      4260
ctgtcaccca ggctggagtg cagtggcgtg atctcggctc actgcaagct ccgcctcccg    4320
ggttcacgcc attctcctgc ctcagcctcc cgagtagctg ggactacagg tgctgccatc    4380
atgcccggct aattttttt tgtattttta gtagagacgg gggtttcacc gtgttagcca    4440
ggatggtctc aatctcctga cctcgtgctc cgccctcctc ggcctcccaa agtgctggga    4500
ttacaggtgt gagacactgc acccaaccac ccagctaatt tttattatt tttatttta     4560 gtagagacag ggtctcagct agttgcccag gctagtcttg gacccttggg ctcaaatgat    4620
tctcccacct ctgcctccca gagtattagg attacaggca taagccactg cccctggcct    4680
ccccaagtga ttgtgatggg cctctctggt taagaaacct caaaattaga gagggagtgg    4740
ggttcaatac tacagcacag gactcagggc aaacaggcct gggttcagat cctggctgtg   4800
ccacttatga actgtgtgat gttaggcaag ttacttaact tatctgagcc ttggttgcct   4860
cttctgtaaa aagggagcta atagatatcc acttttagg aggattgata ttttaaact     4920 gcttagaaca gcccccaaac ataaaaatat ataaataaat cccaactcat gcctagcaga    4980
gggtggatag aggttatttg agggctctgt ccactgtact gggtgacccc tttatggggc    5040
agtggccttt ggccttttta gctgtatgac tcagggcaa gtctcatatc tcttccatct    5100
cctgcccttt aaacttggtg tgaagttacc aagagcctcc tctcccaacc agctgggacg    5160
```

```
tgaaactgtg ggctccactg atcacaagca gtggggtgag gtggggtgga gcagatgtgg    5220
catgtgtccc gggcttcctg cctcatgagg actcagcaga gctttcaccc ccagaaactg    5280
caagttggga cttgtcccta ggaaaatcca gttgctgcca aggtcgtgca gtcactcagc    5340
cctggagtca agccagagca ggcaggtagg tgccagggct ccctcatggg caaactcact    5400
ctccgttttc cctctcctga aggggagga gaggagccag gtagaccagc cacctttaat    5460 tttcttttg cctgcaaaac ggtttccttg gacacaggca acacgaggca ggggctgcca    5520
ggtgtctaga cttcagatca cctgatgtgc ctggcaggat gtggctcagc ctgggagaaa    5580
tcatcccttg cgctgccccg cccggcccct ccttacccct aggccacccg cctgacgaca    5640
tccttgggaa aggccctcag cctacagcac ctgtcagctg ctgtctgaag gaggtagttg    5700
gcagggggaa gtgataggg ggaggctcag taaaactgaa ggcagagagg aataatcata    5760
cttctgtttt caatgcactt ctctatacga agtgctgctg cacgttacc tacattaact    5820 cagttaattc tcatgtctat cctctgagac agtcactatt actatcccca ttttatagat    5880
gaggaaacta gagctcagac aagttaagtt gcttgcccag ggtcacctag taaaacctgg    5940
actccagccc aggtgatctg ctccagagc cctcctgctt aaccaccagg atacagcctt    6000
tcattcagct ctgttctgtc tgccttgctg catggactct gtgatcaatt tcttgagtat    6060
gtgtctgtag ccatgctctt taaacttgta catggcccca tttatggatg aggaaactga    6120
gacctagaga cattaagtgg ctttttaaag cttacgtagt aactggcaga gctaggacca    6180
caacccgggt gcttttttgcc ccaaagtccc gggtacttt acttggcaga gcagggttac    6240
cctacttggg gatctgggtc gggggactta ggaggctgga ggaactgtca gactgtttct    6300
tcttttggga attgaccttc tggccagggc tgcgattagg aaactgctgg actctggcaa    6360
ttcacacata tttggggggc attcacaccc atgagggaca cctctggggg gaaaacaaat    6420
tgattttagc tgataatacc tggtggcaaa caggaccctg gtccttgctc ttgcaataga    6480
cttgcctttg ttgacattag cttgcccttc agttgcctgc tctcccagtg accttggtgt    6540
gccaggctgg ctgagctctg ctggtggggg tcaggcctcc tgtgggaagg aagcaggaag    6600
accagctgga aggagtgaga gagaccctct ggtaggaaga cgtcacctga ggtgacacag    6660
caaagcccgg ccaggtaaca tagtgtctaa tctccgccgt gaccagggcc ttccttgtat    6720
ctctgctgca ggcgccatgt cagaaccggc tggggatgtc cgtcagaacc catgcggcag    6780
caaggcctgc cgccgcctct tcggcccagt ggacagcgag cagctgagcc gcgactgtga    6840
tgcgctaatg gcgggctgca tccaggaggc ccgtgagcga tggaacttcg actttgtcac    6900
cgagacacca ctggagggtg acttcgcctg ggagcgtgtg cggggccttg gcctgcccaa    6960
gctctacctt cccacggggc cccggcgagg ccggatgag ttgggaggag gcaggcggcc    7020
tggcacctca cctgctctgc tgcaggggac agcagaggaa gaccatgtgg acctgtcact    7080
gtcttgtacc cttgtgcctc gctcagggga gcaggctgaa gggtccccag gtggacctgg    7140
agactctcag ggtcgaaaac ggcggcagac cagcatgaca ggtgcggaca tgtgcacgga    7200
aggactttgt aagggaccag gattctcaga atccatggtc caagggctga cctgtctggt    7260
cctggtccag catgctccag gtagaaggaa acaggcccag agagggaag caacctccct    7320 gaggtcacac agcaagtagg cagcaaagac caactagcta acatttattg ggaatgttca    7380
ttatgccagg ccctttgcca agcttctaag gtagatttat ttagtcctta tagcaatgtt    7440
ataacataag acattcttgt cacccctgccc gcctttcttt ttgagacagg tgtcttaact    7500
ctgttggcca gactggagtg cagtgatacg atcatggctc actgcagctt caaactcctg    7560
```

-continued

```
ggctcaagcg atcttcctac ctcagcctcc tgggtagctg ggaagctggg actatagttg    7620
tacaccacta cgcccggtta attttttgag ttttttgtaga dacaaggtct caccatgttg   7680
cccgggctgg tcttgaactc ctgagctcaa gcagtcctcc tgcctcagcc tcccaaagtg   7740
ttgtgattac aggcgtgagc caccatgccc agccccttgc catcctttta gggcaaggaa    7800
accaggctca gagaggtaga gtgatttatc taaggtctca aagtgaattt gccgttgggt   7860
caagactaat tataataaca acaactactg acgtttatat gggcccggca ttgtgctgaa    7920
cactttcatg gattttgtaa cagaatccct agatcagcac tgtccagtaa ctctgcaggg   7980
atgggagtgt ccggtacagg ggccacgagc cacatacggc tgttgtgcat ttgacacaca   8040
gctcatgtga ctgaggaact gaattgttca ttttatttga ttgtagtctg tттааасаад    8100 cacacagagc tagtagtggt tcctctgctg ggcagcttga cttagagcag acccatgggt   8160
gcgggtgcgg tgatggataa aatcacatct gtgaagcatg gtgggacact ccataatacc   8220
cctcaagaga cagagtggac gttccccgag ttcttcctgt tctcagcagt cggccccatt   8280
ggccccaggg aagggtgtcc tggcccccca ctgtcttcct cagttgggca gctccgccgc   8340
gtcctcttct tcttggcctg gctgacttct gctgtctctc ctcagatttc taccactcca   8400
aacgccggct gatcttctcc aagaggaagc cctaatccgc ccacaggaag cctgcagtcc   8460
tggaagcgcg agggcctcaa aagcccgctc tacatcttct gccttagtct cagtttgtgt   8520
gtcttaatta ttatttgtgt tttaatttaa acacctcctc atgtacatac cctggccgcc   8580
ccctgccccc cagcctctgg cattagaatt atttaaacaa aaactaggcg gttgaatgag   8640
aggttcctaa gagtgctggg catttttatt ttatgaaata ctatttaaag cctcctcatc   8700
ccgtgttctc cttttcctct ctcccggagg ttgggtgggc cggcttcatg ccagctactt   8760
cctcctcccc acttgtccgc tgggtggtac cctctggagg ggtgtggctc cttcccatcg   8820
ctgtcacagg cggttatgaa attcaccccc tttcctggac actcagacct gaattctttt   8880
tcatttgaga agtaaacaga tggcactttg aaggggcctc accgagtggg ggcatcatca   8940
aaaactttgg agtcccctca cctcctctaa ggttgggcag ggtgaccctg aagtgagcac   9000
agcctagggc tgagctgggg aactggtacc ctcctggctc ttgatacccc cctctgtctt   9060
gtgaaggcag ggggaaggtg gggtcctgga gcagaccacc ccgcctgccc tcatggcccc   9120
tctgacctgc actggggagc ccgtctcagt gttgagcctt ttccctcttt ggctcccctg   9180
taccttttga ggagccccag ctaccttcct tctccagctg ggctctgcaa ttcccctctg   9240
ctgctgtccc tcccccttgt cctttccctt cagtaccctc tcagctccag gtggctctga   9300
ggtgcctgtc ccacccccac ccccagctca atggactgga aggggaaggg acacacaaga   9360
agaagggcac cctagttcta cctcaggcag ctcaagcagc gaccgccccc tcctctagct   9420 gtggggtga gggtcccatg tggtggcaca ggcccccttg agtgggggtta tctctgtgtt    9480 agggtatat gatgggggag tagatctttc taggaggggag acactggccc ctcaaatcgt   9540
ccagcgacct tcctcatcca ccccatccct ccccagttca ttgcactttg attagcagcg   9600
gaacaaggag tcagacattt taagatggtg gcagtagagg ctatggacag ggcatgccac   9660
gtgggctcat atgggctgg gagtagttgt ctttcctggc actaacgttg agcccctgga   9720
ggcactgaag tgcttagtgt acttggagta ttggggtctg accccaaaca ccttccagct   9780
cctgtaacat actggcctgg actgttttct ctcggctccc catgtgtcct ggttcccgtt   9840
tctccaccta gactgtaaac ctctcgaggg cagggaccac accctgtact gttctgtgtc   9900
```

-continued

```
tttcacagct cctcccacaa tgctgaatat acagcaggtg ctcaataaat gattcttagt    9960
gactttactt gtaatattac tattgtggtt attatacctt ataagaacaa ataaatgggc   10020
ttttgggaag gatttcataa ttaaataatt ttaaaaatta agcatttaaa tttagagaat   10080
gcagaaaact tagcaaacag aaagactgct gcaaaaaaca acagcaaaac aaaaactact   10140
gtcacacctc tgcaaagatc accaatgtca atattttggt tgttgtgta atcttttttgt   10200 aaagaatata ttatagctta acatcattat tcatcagata aatgcaaatt aagataccac   10260
aataagatac caccatacac ttaccagaat gattaaaaaa gactgacagt gccaagcatt   10320
ggcaaggtta tggagcaact ggatctctta tttaaaaaaa ctgtttgggc cgggcgcagt   10380
ggctcacacc tagaatccca gtgcttcggg aggctgaggc aggagatcac ttgaggccaa   10440
gggttcaaga ccagcctggc caacatggtg aaatctctac taaaaataca aaaattagct   10500
gggcatggtg gtgcacgctt gtaatcccag ctacttggaa ggctgaggtg gaggatcac   10560 ttgaacccag gaggcagagg ttgcagtcag ctgagatcat accactgtac tccagcctct   10620
tccagggtga cagtgagatt catctcaaat aaatacataa ataaaaaact gtttggtaat   10680
atcttctaaa gatgcctacc ttcatggcta cctcatgacc cagtaattct attcctggac   10740
atgttctcga gagaaatgag ttcatatttc cactgaaaaa ggcataagaa tgttctacac   10800
agtggctcac acctataatc ccagcacttt gggaggctaa ggcaggagga cggcttgagc   10860
ccaagagtgt gagaccagtt tgggcaacat agcgagactc ttatctc                 10907
```

<210> SEQ ID NO 17
<211> LENGTH: 164
<212> TYPE: PRT
<213> ORGANISM: homo sapiens

<400> SEQUENCE: 17

```
Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro
```